(12) United States Patent
Fauber et al.

(10) Patent No.: US 8,912,219 B2
(45) Date of Patent: Dec. 16, 2014

(54) ARYL SULFAMIDE AND SULFAMATE DERIVATIVES AS RORC MODULATORS

(71) Applicant: Genentech, Inc., South San Francisco, CA (US)

(72) Inventors: Benjamin Fauber, San Francisco, CA (US); Olivier Rene, San Francisco, CA (US); Monique Bodil van Niel, Harlow (GB); Stuart Ward, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/210,978

(22) Filed: Mar. 14, 2014

(65) Prior Publication Data
US 2014/0275032 A1    Sep. 18, 2014

Related U.S. Application Data

(60) Provisional application No. 61/790,271, filed on Mar. 15, 2013.

(51) Int. Cl.
| A61K 31/445 | (2006.01) |
| C07D 211/96 | (2006.01) |
| C07D 285/36 | (2006.01) |
| C07D 295/185 | (2006.01) |
| C07D 417/12 | (2006.01) |
| C07D 285/16 | (2006.01) |

(52) U.S. Cl.
CPC ............ *C07D 417/12* (2013.01); *C07D 285/36* (2013.01); *C07D 295/185* (2013.01); *C07D 285/16* (2013.01); *C07D 211/96* (2013.01)

USPC ........... 514/327; 546/184; 546/192; 546/216; 514/315; 514/317

(58) Field of Classification Search
CPC ............................ A61K 31/445; C07D 211/96
USPC ........... 546/184, 192, 216; 514/315, 317, 327
See application file for complete search history.

(56) References Cited

U.S. PATENT DOCUMENTS 8,178,532 B2 *  5/2012  Bannen et al. ............. 514/237.2
8,497,284 B2 *  7/2013  Bannen et al. ................ 514/312

* cited by examiner

Primary Examiner — Golam M M Shameem
(74) Attorney, Agent, or Firm — Robert C. Hall

(57) ABSTRACT

Compounds of the formula I:

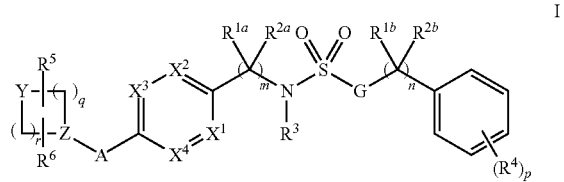

or pharmaceutically acceptable salts thereof,
wherein m, n, p, q, r, A, $X^1$, $X^2$, $X^3$, $X^4$, $X^5$, $X^6$, Y, Z, G, $R^{1a}$, $R^{2a}$, $R^{1b}$, $R^{2b}$, $R^3$, $R^4$, $R^5$ and $R^6$ are as defined herein. Also disclosed are methods of making the compounds and using the compounds for treatment of inflammatory diseases such as arthritis.

20 Claims, No Drawings

ARYL SULFAMIDE AND SULFAMATE DERIVATIVES AS RORC MODULATORS

CROSS REFERENCE TO RELATED APPLICATIONS

This application claims the benefit of priority of U.S. Provisional Patent Application Ser. No. 61/790,271, filed Mar. 15, 2013, the disclosure of which is incorporated herein by reference in their entirety.

FIELD OF THE INVENTION

The invention pertains to compounds that modulate the function of retinoid-receptor related orphan receptor RORc (RORγ) and use of such compounds for treatment of autoimmune diseases

BACKGROUND OF THE INVENTION

T helper 17 cells (Th17) are interleukin (IL)-17 secreting CD4+ T cells involved in pathogenesis of autoimmune diseases such as rheumatoid arthritis, irritable bowel disease, psoriasis, psoriatic arthritis and spondyloarthridities. The retinoic acid-related orphan receptor γ (RORγ or RORc) is recognized as a transcription factor necessary for Th17 cell differentiation. RORc is an orphan member of the nuclear hormone receptor subfamily that includes RORα (RORa) and RORβ (RORb). RORc controls gene transcription by binding to DNA as a monomer. Selective modulation of RORc has been proposed as a route to discovery and development of Th17 cell-associated autoimmune diseases.

There is accordingly a need for compounds that inhibit RORc for use in treatment of autoimmune diseases such as rheumatoid arthritis, irritable bowel disease, psoriasis, psoriatic arthritis and spondyloarthridities.

SUMMARY OF THE INVENTION

The invention provides compounds of the formula I:

or a pharmaceutically acceptable salt thereof,
wherein:
m is 0 or 1
n is 0 or 1
p is from 0 to 3;
q is 1 or 2;
r is from 1 to 3;
A is: a bond; —$CH_2$—; —C(O)—; —$NR^a$—; —C(O)$NR^a$—$(CH_2)_t$—; —$(CH_2)_t$—$NR^aC(O)$—; —O—; —S—; or —$SO_2$—;
t is from 0 to 4;
one of $X^1$, $X^2$, $X^3$ and $X^4$ is N and the others are $CR^b$; or two of $X^1$, $X^2$, $X^3$ and $X^4$ are N and the others are $CR^b$; or three of $X^1$, $X^2$, $X^3$ and $X^4$ are N and the other is $CR^b$; or each of $X^1$, $X^2$, $X^3$ and $X^4$ is $CR^b$;
Y is: —O—; —S—; $SO_2$—; —$CR^cR^d$—; or —$NR^e$—;
Z is: CH; or N;
G is: —$NR^f$—; or —O—;

$R^{1a}$, $R^{2a}$, $R^{1b}$ and $R^{2b}$ each independently is: hydrogen; or $C_{1-6}$alkyl which may be unsubstituted or substituted one or more times with halo;

$R^3$ is: hydrogen; $C_{1-6}$alkyl; $C_{3-6}$cycloalkyl; $C_{3-6}$cycloalkyl-$C_{1-6}$alkyl; $C_{1-6}$alkoxy-$C_{1-6}$alkyl; or hydroxy-$C_{1-6}$alkyl, wherein the $C_{1-6}$alkyl and $C_{3-6}$cycloalkyl moieties may be substituted one or more times with halo;

each $R^4$ is independently: $C_{1-6}$alkyl; halo; $C_{1-6}$alkoxy; or cyano; wherein the $C_{1-6}$alkyl moieties may be unsubstituted or substituted one or more times with halo;

$R^5$ is: hydrogen; halo; or $C_{1-6}$alkyl which may be unsubstituted or substituted one or more times with halo;

$R^6$ is: hydrogen; halo; carboxy; $C_{1-6}$alkyl-carbonyl; $C_{1-6}$alkoxy-carbonyl; oxo; hydroxy; aminocarbonyl; N—$C_{1-6}$alkyl-aminocarbonyl; N,N-di-$C_{1-6}$alkyl-aminocarbonyl; or $C_{1-6}$alkyl which may be unsubstituted or substituted one or more times with halo; or oxo;

or $R^5$ and $R^6$ together with the atoms to which they are attached may form a four, five, six or seven membered ring;

$R^a$ is: hydrogen; or $C_{1-6}$alkyl which may be unsubstituted or substituted one or more times with halo;

each $R^b$ is independently: hydrogen; $C_{1-6}$alkyl; halo; $C_{1-6}$alkoxy; or cyano; wherein the $C_{1-6}$alkyl moieties may be unsubstituted or substituted one or more times with halo;

$R^c$ is: hydrogen; halo; or $C_{1-6}$alkyl which may be unsubstituted or substituted one or more times with halo;

$R^d$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; carboxy; N-cyano-aminocarbonyl; N-cyano-N-$C_{1-6}$alkyl-aminocarbonyl; N-$C_{1-6}$alkyl-acetimidamidyl; N,N'-di-$C_{1-6}$alkyl-acetimidamidyl; N'-cyano-N-$C_{1-6}$alkyl-acetimidamidyl; N'-hydroxy-acetimidamidyl; N'-$C_{1-6}$alkoxy-acetimidamidyl; N'-hydroxy-N-$C_{1-6}$alkyl-acetimidamidyl; N-$C_{1-6}$alkoxy-N-$C_{1-6}$alkyl-acetimidamidyl; 2-nitro-1-N-$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N-$C_{1-6}$alkoxy-aminocarbonyl; N-$C_{1-6}$alkyl-aminocarbonyl; N-hydroxy-N-$C_{1-6}$alkyl-aminocarbonyl; N-$C_{1-6}$alkoxy-N-$C_{1-6}$alkyl-aminocarbonyl; N,N-di-$C_{1-6}$alkyl-aminocarbonyl; aminosulfonyl; N-$C_{1-6}$alkyl-aminosulfonyl; N,N-di-$C_{1-6}$alkyl-aminosulfonyl; cyano; $C_{1-6}$alkoxy; $C_{1-6}$alkyl-sulfonylamino; N-$C_{1-6}$alkyl-sulfonylaminocarbonyl; N-($C_{1-6}$alkyl-sulfonyl)-N-$C_{1-6}$alkyl-aminocarbonyl; N-($C_{1-6}$alkyl-sulfonyl)-amino-$C_{1-6}$alkyl; amino; N-$C_{1-6}$alkyl-amino; N,N-di-$C_{1-6}$alkyl-amino; halo-$C_{1-6}$alkyl; heterocyclyl; heteroaryl; or hydroxyl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^g$;

or $R^c$ and $R^d$ together with the atoms to which they are attached may form a four, five, six or seven membered ring that may optionally include one or two heteroatoms selected from —O—, —$NR^a$— or —S—, and which may be optionally substituted one or more times with $R^g$;

$R^e$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; N-cyano-aminocarbonyl; N-cyano-N-$C_{1-6}$alkyl-aminocarbonyl; N-$C_{1-6}$alkyl-acetimidamidyl; N,N'-di-$C_{1-6}$alkyl-acetimidamidyl; N'-cyano-N-$C_{1-6}$alkyl-acetimidamidyl; N'-hydroxy-acetimidamidyl;

N'-$C_{1-6}$alkoxy-acetimidamidyl; N'-hydroxy-N-$C_{1-6}$alkyl-acetimidamidyl; N'-$C_{1-6}$alkoxy-N-$C_{1-6}$alkyl-acetimidamidyl; 2-nitro-1-N-$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N-$C_{1-6}$alkoxy-aminocarbonyl; N-$C_{1-6}$alkyl-aminocarbonyl; N-hydroxy-N-$C_{1-6}$alkyl-aminocarbonyl; N-$C_{1-6}$alkoxy-N-$C_{1-6}$alkyl-aminocarbonyl; N,N-di-$C_{1-6}$alkyl-aminocarbonyl; aminosulfonyl; N-$C_{1-6}$alkyl-aminosulfonyl; N,N-di-$C_{1-6}$alkyl-aminosulfonyl; cyano; $C_{1-6}$alkyl-sulfonylamino; $C_{1-6}$alkyl-sulfonylamino-$C_{1-6}$alkyl; N-($C_{1-6}$alkyl-sulfonyl)aminocarbonyl; N-($C_{1-6}$alkyl-sulfonyl)-N-$C_{1-6}$alkyl-aminocarbonyl; N-($C_{1-6}$alkyl-sulfonyl)-amino-$C_{1-6}$alkyl; halo-$C_{1-6}$alkyl; heterocyclyl; or heteroaryl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^g$;

or $R^e$ and one of $R^5$ and $R^6$ together with the atoms to which they are attached may form a four, five, six or seven membered ring that may optionally include one or two additional heteroatom selected from —O—, —$NR^a$— or —S—, and which may be optionally substituted one or more times with $R^g$;

or one of $R^c$ and $R^d$ and one of $R^5$ and $R^6$ together with the atoms to which they are attached may form a four, five, six or seven membered ring that may optionally include an additional heteroatom selected from —O—, —$NR^a$— or —S—, and which may be optionally substituted one or more times with $R^g$;

$R^f$ is: hydrogen; $C_{1-6}$alkyl; $C_{3-6}$cycloalkyl; $C_{3-6}$cycloalkyl-$C_{1-6}$alkyl; $C_{1-6}$alkoxy-$C_{1-6}$alkyl; or hydroxy-$C_{1-6}$alkyl, wherein the $C_{1-6}$alkyl and $C_{3-6}$cycloalkyl moieties may be substituted one or more times with halo;

or $R^f$ and $R^3$ together with the atoms to which they are attached may form a five, six or seven membered ring that may be optionally substituted one or more times with $R^h$;

$R^g$ is: $C_{1-6}$alkyl; halo; oxo; hydroxy; acetyl; or $C_{1-6}$alkoxy; wherein the $C_{1-6}$alkyl moieties may be unsubstituted or substituted one or more times with halo; and $R^h$ is: $C_{1-6}$alkyl; halo; oxo; hydroxy; acetyl; or $C_{1-6}$alkoxy; wherein the $C_{1-6}$alkyl moieties may be unsubstituted or substituted one or more times with halo;

or two of $R^h$ together with the atoms to which they are attached may form a four, five, six or seven membered ring that may optionally include an additional heteroatom selected from —O—, —$NR^a$— or —S—, and which may be optionally substituted one or more times with $R^g$.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy' means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxyalkylcarbonyl" means a moiety of the formula —C(O)—R—R', wherein R is alkylene and R' is alkoxy as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —$SO_2$—R, wherein R is alkyl as defined herein.

"Alkylsulfonylalkyl means a moiety of the formula —R'—$SO_2$—R" where where R' is alkylene and R" is alkyl as defined herein.

"Alkylsulfonylalkoxy" means a group of the formula —O—R—$SO_2$—R' wherein R is alkylene and R' is alkyl as defined herein.

"Amino means a moiety of the formula —NRR' wherein R and R' each independently is hyrdogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"N-hydroxy-aminocarbonyl" means a group of the formula —C(O)—NH—OH.

"N-alkoxy-aminocarbonyl" means a group of the formula —C(O)—NH—R wherein R is alkoxy as defined herein.

"N-alkyl-aminocarbonyl means a group of the formula —C(O)—NH—R wherein R is alkyl as defined herein.

"N-hydroxy-N-alkylaminocarbonyl means a group of the formula —C(O)—NRR' wherein R is alkyl as defined herein and R' is hydroxy.

"N-alkoxy-N-alkylaminocarbonyl" means a group of the formula —C(O)—NRR' wherein R is alkyl and R' is alkoxy as defined herein.

"N,N-di-$C_{1-6}$alkyl-aminocarbonyl" means a group of the formula —C(O)—NRR' wherein R and R' are alkyl as defined herein.

"Aminosulfonyl" means a group of the formula —$SO_2$—$NH_2$.

"N-alkylaminosulfonyl" means a group of the formula —$SO_2$—NHR wherein R is alkyl as defined herein.

"N,N-dialkylaminosulfonyl" means a group of the formula —$SO_2$—NRR' wherein R and R' are alkyl as defined herein.

"Alkylsulfonylamino" means a group of the formula —NH—$SO_2$—R wherein R is alkyl as defined herein.

"N-(alkylsulfonyl)-aminoalkyl" means a group of the formula —R—NH—$SO_2$—R' wherein R is alkylene and R' is alkyl as defined herein.

"N-(Alkylsulfonyl)aminocarbonyl" means a group of the formula —C(O)—NH—$SO_2$—R wherein wherein R is alkyl as defined herein.

"N-(Alkylsulfonyl)-N-alkylaminocarbonyl" means a group of the formula —C(O)—NR—$SO_2$—R' wherein wherein R and R' are alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"N-Alkylacetimidamidyl" means a group of the formula

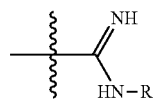

wherein R is alkyl as defined herein.

"N,N'-Dialkylacetimidamidyl" means a group of the formula

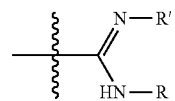

wherein
R and R' are both alkyl as defined herein.

"N'-Alkoxyacetimidamidyl" means a group of the formula

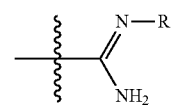

wherein R is alkoxy as defined herein.

"N'-Alkoxy-N-alkyl-acetimidamidyl" means a group of the formula

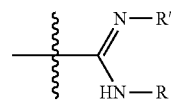

wherein R is alkyl and R' is alkoxy as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl"" means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substitued with one or more substituents, wherein each substituent is independently hydroxy, alkyl, alkoxy, halo, haloalkyl, amino, monoalkylamino, or dialkylamino. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkenyl" means a cycloalkyl as defined herein that includes at least one double bond or unsaturation. Exemplary cycloalkenyl include cyclohexenyl, cyclopentenyl, cyclobutenyl and the like.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Cycloalkylcarbonyl" means a moiety of the formula —C(O)—R, wherein R is cycloalkyl as defined herein.

"$C_{3-6}$cycloalkyl-$C_{1-6}$alkyl-carbonyl" means a moiety of the formula —C(O)—R, wherein R is cycloalkylalkyl as defined herein.

"Cyanoalkylcarbonyl" means a moiety of the formula —C(O)—R—R', wherein R is alkylene as defined herein and R' is cyano or nitrile.

"N-Cyano-aminocarbonyl" means a moiety of the formula —C(O)—NHR, wherein R is cyano or nitrile.

"N-Cyano-N-alkyl-aminocarbonyl" means a moiety of the formula —C(O)—NRR'—R, wherein R' is alkyl as defined herein and R is cyano or nitrile.

"Cycloalkylsulfonyl" means a group of the formula —SO$_2$—R wherein R is cycloalkyl as defined herein.

"Cycloalkylalkylsulfonyl" means a group of the formula —SO$_2$—R wherein R is cycloalkylalkyl as defined herein.

"N'-Cyanoacetimidamidyl" means a group of the formula

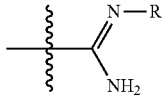

wherein R is cyano or nitrile.

"N'-Cyano-N-alkylacetimidamidyl" means a group of the formula

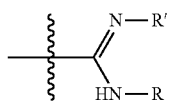

wherein R is alkyl as defined herein and R' is cyano or nitrile.

"Formyl" means a moiety of the formula —C(O)—H.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

"Heteroarylalkyl" or "heteroaralkyl" means a group of the formula —R—R' wherein R is alkylene and R' is heteroaryl as defined herein.

"Heteroarylsulfonyl" means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkylcarbonyl" means a moiety of the formula —C(O)—R—R', wherein R is alkylene as defined herein and R' is hydroxy.

"N'hydroxyacetimidamidyl" means a group of the formula

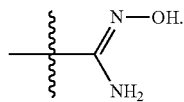

"N'-hydroxy-N-alkyl-acetimidamidyl" means a group of the formula

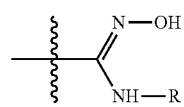

wherein R is alkyl as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"2-Nitro-1-N-alkylamino-vinyl" means a group of the formula

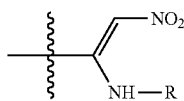

wherein R is alkyl as defined herein.

"Oxo" means a group of the formula =O (i.e., an oxygen with a double bond). Thus, for example, a 1-oxo-ethyl group is an acetyl group.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfamide" means a group of the general formula

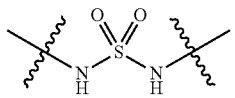

wherein the hydrogens shown on the nitrogen atoms may be substituted with various groups as described herein (see, e.g., the description for groups $R^3$ and $R^f$ in formula I).

"Sulfamate" means a group of the general formula

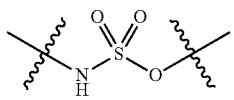

wherein the hydrogen shown on the nitrogen atom may be substituted with various groups as described herein (see, e.g., the description for groups $R^3$ in formula I).

"Sulfonamido" means a group of the formula —SO$_2$—NR'R" wherein R', R" and R'" each independently is hydrogen or alkyl.

"Optionally substituted" when used in association with an "aryl", phenyl", "heteroaryl" "cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Arthritis" means a disease or condition that causes damage to joints of the body and pain associated with such joint damage. Arthritis includes rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

"Respiratory disorder" refers to, without limitation, chronic obstructive pulmonary disease (COPD), asthma, bronchospasm, and the like.

"Gastrointestinal disorder" ("GI disorder") refers to, without limitation, Irritable Bowel Syndrome (IBS), Inflammatory Bowel Disease (IBD), biliary colic and other biliary disorders, renal colic, diarrhea-dominant IBS, pain associated with GI distension, and the like.

"Pain" includes, without limitation, inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature and chemical names used in this Application are based on ChembioOffice™ by CambridgeSoft™. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes. One or more carbon atom(s) of a compound of the invention may be replaced by a silicon atom(s), and it is contemplated that one or more oxygen atom(s) of a compound of the invention may be replaced by a sulfur or selenium atom(s).

Compounds of the Invention

The invention provides compounds of the formula I:

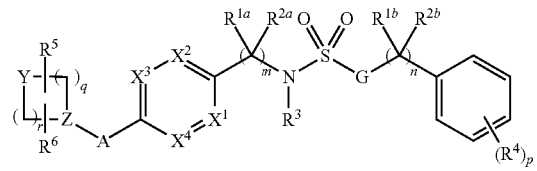

or a pharmaceutically acceptable salt thereof,
wherein:
m is 0 or 1
n is 0 or 1
p is from 0 to 3;
q is 1 or 2;
r is from 1 to 3;

A is: a bond; —$CH_2$—; —C(O)—; —$NR^a$—; —C(O)$NR^a$—$(CH_2)_t$—; —$(CH_2)_t$—$NR^aC(O)$—; —O—; —S—; or —$SO_2$—;

t is from 0 to 4;

one of $X^1$, $X^2$, $X^3$ and $X^4$ is N and the others are $CR^b$; or two of $X^1$, $X^2$, $X^3$ and $X^4$ are N and the others are $CR^b$; or three of $X^1$, $X^2$, $X^3$ and $X^4$ are N and the other is $CR^b$; or each of $X^1$, $X^2$, $X^3$ and $X^4$ is $CR^b$;

Y is: —O—; —S—; $SO_2$—; —$CR^cR^d$—; or —$NR^e$—;

Z is: CH; or N;

G is: —$NR^f$—; or —O—;

$R^{1a}$, $R^{2a}$, $R^{1b}$ and $R^{2b}$ each independently is: hydrogen; or $C_{1-6}$alkyl which may be unsubstituted or substituted one or more times with halo;

$R^3$ is: hydrogen; $C_{1-6}$alkyl; $C_{3-6}$cycloalkyl; $C_{3-6}$cycloalkyl-$C_{1-6}$alkyl; $C_{1-6}$alkoxy-$C_{1-6}$alkyl; or hydroxy-$C_{1-6}$alkyl, wherein the $C_{1-6}$alkyl and $C_{3-6}$cycloalkyl moieties may be substituted one or more times with halo;

each $R^4$ is independently: $C_{1-6}$alkyl; halo; $C_{1-6}$alkoxy; or cyano; wherein the $C_{1-6}$alkyl moieties may be unsubstituted or substituted one or more times with halo;

$R^5$ is: hydrogen; halo; or $C_{1-6}$alkyl which may be unsubstituted or substituted one or more times with halo;

$R^6$ is: hydrogen; halo; carboxy; $C_{1-6}$alkyl-carbonyl; $C_{1-6}$alkoxy-carbonyl; oxo; hydroxy; aminocarbonyl; N-$C_{1-6}$alkyl-aminocarbonyl; N,N-di-$C_{1-6}$alkyl-aminocarbonyl; or $C_{1-6}$alkyl which may be unsubstituted or substituted one or more times with halo; or oxo;

or $R^5$ and $R^6$ together with the atoms to which they are attached may form a four, five, six or seven membered ring;

$R^a$ is: hydrogen; or $C_{1-6}$alkyl which may be unsubstituted or substituted one or more times with halo;

each $R^b$ is independently: hydrogen; $C_{1-6}$alkyl; halo; $C_{1-6}$alkoxy; or cyano; wherein the $C_{1-6}$alkyl moieties may be unsubstituted or substituted one or more times with halo;

$R^c$ is: hydrogen; halo; or $C_{1-6}$alkyl which may be unsubstituted or substituted one or more times with halo;

$R^d$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; carboxy; N-cyano-aminocarbonyl; N-cyano-N-$C_{1-6}$alkyl-aminocarbonyl; N-$C_{1-6}$alkyl-acetimidamidyl; N,N'-di-$C_{1-6}$alkyl-acetimidamidyl; N'-cyano-N-$C_{1-6}$alkyl-acetimidamidyl; N'-hydroxy-acetimidamidyl; N'-$C_{1-6}$alkoxy-acetimidamidyl; N'-hydroxy-N-$C_{1-6}$alkyl-acetimidamidyl; N-$C_{1-6}$alkoxy-N-$C_{1-6}$alkyl-acetimidamidyl; 2-nitro-1-N-$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N-$C_{1-6}$alkoxy-aminocarbonyl; N-$C_{1-6}$alkyl-aminocarbonyl; N-hydroxy-N-$C_{1-6}$alkyl-aminocarbonyl; N-$C_{1-6}$alkoxy-N-$C_{1-6}$alkyl-aminocarbonyl; N,N-di-$C_{1-6}$alkyl-aminocarbonyl; aminosulfonyl; N-$C_{1-6}$alkyl-aminosulfonyl; N,N-di-$C_{1-6}$alkyl-aminosulfonyl; cyano; $C_{1-6}$alkoxy; $C_{1-6}$alkyl-sulfonylamino; N-$C_{1-6}$alkyl-sulfonylaminocarbonyl; N-($C_{1-6}$alkyl-sulfonyl)-N-$C_{1-6}$alkyl-aminocarbonyl; N-($C_{1-6}$alkyl-sulfonyl)-amino-$C_{1-6}$alkyl; amino; N-$C_{1-6}$alkyl-amino; N,N-di-$C_{1-6}$alkyl-amino; halo-$C_{1-6}$alkyl; heterocyclyl; heteroaryl; or hydroxyl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^g$;

or $R^c$ and $R^d$ together with the atoms to which they are attached may form a four, five, six or seven membered ring that may optionally include one or two heteroatoms selected from —O—, —$NR^a$— or —S—, and which may be optionally substituted one or more times with $R^g$;

$R^e$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; N-cyano-aminocarbonyl; N-cyano-N-$C_{1-6}$alkyl-aminocarbonyl; N-$C_{1-6}$alkyl-acetimidamidyl; N,N'-di-$C_{1-6}$alkyl-acetimidamidyl; N'-cyano-N-$C_{1-6}$alkyl-acetimidamidyl; N'-hydroxy-acetimidamidyl; N'-$C_{1-6}$alkoxy-acetimidamidyl; N'-hydroxy-N-$C_{1-6}$alkyl-acetimidamidyl; N'-$C_{1-6}$alkoxy-N-$C_{1-6}$alkyl-acetimidamidyl; 2-nitro-1-N-$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N-$C_{1-6}$alkoxy-aminocarbonyl; N-$C_{1-6}$alkyl-aminocarbonyl; N-hydroxy-N-$C_{1-6}$alkyl-aminocarbonyl; N-$C_{1-6}$alkoxy-N-$C_{1-6}$alkyl-aminocarbonyl; N,N-di-$C_{1-6}$alkyl-aminocarbonyl; aminosulfonyl; N-$C_{1-6}$alkyl-aminosulfonyl; N,N-di-$C_{1-6}$alkyl-aminosulfonyl; cyano; $C_{1-6}$alkyl-sulfonylamino; $C_{1-6}$alkyl-sulfonylamino-$C_{1-6}$alkyl; N-($C_{1-6}$alkyl-sulfonyl)aminocarbonyl; N-($C_{1-6}$alkyl-sulfonyl)-N-$C_{1-6}$alkyl-aminocarbonyl; N-($C_{1-6}$alkyl-sulfonyl)-amino-$C_{1-6}$alkyl; halo-$C_{1-6}$alkyl; heterocyclyl; or heteroaryl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^g$;

or $R^e$ and one of $R^5$ and $R^6$ together with the atoms to which they are attached may form a four, five, six or seven membered ring that may optionally include one or two additional heteroatom selected from —O—, —$NR^a$— or —S—, and which may be optionally substituted one or more times with $R^g$;

or one of $R^c$ and $R^d$ and one of $R^5$ and $R^6$ together with the atoms to which they are attached may form a four, five, six or seven membered ring that may optionally include an additional heteroatom selected from —O—, —$NR^a$— or —S—, and which may be optionally substituted one or more times with $R^g$;

$R^f$ is: hydrogen; $C_{1-6}$alkyl; $C_{3-6}$cycloalkyl; $C_{3-6}$cycloalkyl-$C_{1-6}$alkyl; $C_{1-6}$alkoxy-$C_{1-6}$alkyl; or hydroxy-$C_{1-6}$alkyl, wherein the $C_{1-6}$alkyl and $C_{3-6}$cycloalkyl moieties may be substituted one or more times with halo; or $R^f$ and $R^3$ together with the atoms to which they are attached may form a five, six or seven membered ring that may be optionally substituted one or more times with $R^h$;

$R^g$ is: $C_{1-6}$alkyl; halo; oxo; hydroxy; acetyl; or $C_{1-6}$alkoxy; wherein the $C_{1-6}$alkyl moieties may be unsubstituted or substituted one or more times with halo; and $R^h$ is: $C_{1-6}$alkyl; halo; oxo; hydroxy; acetyl; or $C_{1-6}$alkoxy; wherein the $C_{1-6}$alkyl moieties may be unsubstituted or substituted one or more times with halo;

or two of $R^h$ together with the atoms to which they are attached may form a four, five, six or seven membered ring that may optionally include an additional heteroatom selected from —O—, —$NR^a$— or —S—, and which may be optionally substituted one or more times with $R^g$.

In certain embodiments of formula I, when A is a heteroatom, then X is —CH—.

In certain embodiments of formula I, m is 0.

In certain embodiments of formula I, m is 1.

In certain embodiments of formula I, n is 0.

In certain embodiments of formula I, n is 1.

In certain embodiments of formula I, p is from 0 to 2.

In certain embodiments of formula I, p is 0 or 1.
In certain embodiments of formula I, p is 0.
In certain embodiments of formula I, p is 1.
In certain embodiments of formula I, p is 2.
In certain embodiments of formula I, p is 3.
In certain embodiments of formula I, q is 1.
In certain embodiments of formula I, q is 2.
In certain embodiments of formula I, r is 1.
In certain embodiments of formula I, r is 2.
In certain embodiments of formula I, r is 3.
In certain embodiments of formula I, t is from 0 to 3.
In certain embodiments of formula I, t is 0.
In certain embodiments of formula I, t is 1.
In certain embodiments of formula I, t is 2.
In certain embodiments of formula I, t is 3.
In certain embodiments of formula I, A is: a bond; —$CH_2$—; —C(O)—; —$NR^a$—; —O—; —S—; or —$SO_2$—.
In certain embodiments of formula I, A is: a bond; —$NR^a$—; —O—; or —S—.
In certain embodiments of formula I, A is: a bond; —$NR^a$—; or —O—.
In certain embodiments of formula I, A is a bond.
In certain embodiments of formula I, A is —$CH_2$—.
In certain embodiments of formula I, A is —C(O)—.
In certain embodiments of formula I, A is —$NR^a$—.
In certain embodiments of formula I, A is —O—.
In certain embodiments of formula I, A is —S—.
In certain embodiments of formula I, A is —$SO_2$—.
In certain embodiments of formula I, A is: —C(O)$NR^a$—($CH_2$)—.
In certain embodiments of formula I, A is: —$(CH_2)_t$—$NR^aC(O)$—.
In certain embodiments of formula I, one or two of $X^1$, $X^2$, $X^3$ and $X^4$ is N and the others are $CR^b$.
In certain embodiments of formula I, three of $X^1$, $X^2$, $X^3$ and $X^4$ are $CR^b$ and the other is N.
In certain embodiments of formula I, $X^1$, $X^2$, $X^3$ and $X^4$ are $CR^b$.
In certain embodiments of formula I, $X^1$ is N and $X^2$, $X^3$ and $X^4$ are $CR^b$.
In certain embodiments of formula I, $X^2$ is N and $X^1$, $X^3$ and $X^4$ are $CR^b$.
In certain embodiments of formula I, $X^1$ and $X^4$ are N, and $X^2$ and $X^3$ are $CR^b$.
In certain embodiments of formula I, $X^2$ and $X^3$ are N, and $X^1$ and $X^4$ are $CR^b$.
In certain embodiments of formula I, $X^1$ and $X^2$ are N, and $X^3$ and $X^4$ are $CR^b$.
In certain embodiments of formula I, Y is —O—, —$CR^cR^d$— or —$NR^e$—.
In certain embodiments of formula I, Y is —$CR^cR^d$— or —$NR^e$—.
In certain embodiments of formula I, Y is —O—.
In certain embodiments of formula I, Y is —S—.
In certain embodiments of formula I, Y is —$SO_2$—.
In certain embodiments of formula I, Y is —$CR^cR^d$—.
In certain embodiments of formula I, Y is —$NR^e$—.
In certain embodiments of formula I, Z is CH.
In certain embodiments of formula I, Z is N.
In certain embodiments of formula I, G is —$NR^f$—.
In certain embodiments of formula I, G is —O—.
In certain embodiments of formula I, each $R^1$ is independently: $C_{1-6}$alkyl; halo; $C_{1-6}$alkoxy; cyano; halo-$C_{1-6}$alkyl; or halo-$C_{1-6}$alkoxy.
In certain embodiments of formula I, $R^{1a}$ is hydrogen.
In certain embodiments of formula I, $R^{1a}$ is $C_{1-6}$alkyl.
In certain embodiments of formula I, $R^{2a}$ is hydrogen.
In certain embodiments of formula I, $R^{2a}$ is $C_{1-6}$alkyl.
In certain embodiments of formula I, $R^{1b}$ is hydrogen.
In certain embodiments of formula I, $R^{1b}$ is $C_{1-6}$alkyl.
In certain embodiments of formula I, $R^{2b}$ is hydrogen.
In certain embodiments of formula I, $R^{2b}$ is $C_{1-6}$alkyl.
In certain embodiments of formula I, $R^3$ is hydrogen.
In certain embodiments of formula I, $R^3$ is $C_{1-6}$alkyl.
In certain embodiments of formula I, $R^3$ is halo-$C_{1-6}$alkyl.
In certain embodiments of formula I, $R^3$ is $C_{3-6}$cycloalkyl.
In certain embodiments of formula I, $R^3$ is $C_{3-6}$cycloalkyl-$C_{1-6}$alkyl.
In certain embodiments of formula I, $R^3$ is $C_{1-6}$alkoxy-$C_{1-6}$alkyl.
In certain embodiments of formula I, $R^3$ is hydroxy-$C_{1-6}$alkyl.
In certain embodiments of formula I, each $R^4$ is independently: $C_{1-6}$alkyl; halo; or halo-$C_{1-6}$alkyl.
In certain embodiments of formula I, $R^4$ is $C_{1-6}$alkyl.
In certain embodiments of formula I, $R^4$ is halo.
In certain embodiments of formula I, $R^4$ is $C_{1-6}$alkoxy.
In certain embodiments of formula I, $R^4$ is cyano.
In certain embodiments of formula I, $R^4$ is halo-$C_{1-6}$alkyl.
In certain embodiments of formula I, each $R^4$ is independently: fluoro; chloro; or trifluoromethyl.
In certain embodiments of formula I, $R^5$ is: hydrogen or $C_{1-6}$alkyl.
In certain embodiments of formula I, $R^5$ is hydrogen.
In certain embodiments of formula I, $R^5$ is $C_{1-6}$alkyl.
In certain embodiments of formula I, $R^5$ is halo.
In certain embodiments of formula I, $R^6$ is: hydrogen; halo; oxo; hydroxy; or $C_{1-6}$alkyl which may be unsubstituted or substituted one or more times with halo; or oxo.
In certain embodiments of formula I, $R^6$ is: hydrogen; halo; or $C_{1-6}$alkyl.
In certain embodiments of formula I, $R^6$ is: hydrogen; $C_{1-6}$alkyl; or halo.
In certain embodiments of formula I, $R^6$ is: hydrogen; or $C_{1-6}$alkyl.
In certain embodiments of formula I, $R^6$ is hydrogen.
In certain embodiments of formula I, $R^6$ is $C_{1-6}$alkyl.
In certain embodiments of formula I, $R^6$ is halo.
In certain embodiments of formula I, $R^6$ is oxo.
In certain embodiments of formula I, $R^5$ and $R^6$ together with the atoms to which they are attached form a four, five, six or seven membered ring.
In certain embodiments of formula I, $R^a$ is hydrogen.
In certain embodiments of formula I, $R^a$ is $C_{1-6}$alkyl.
In certain embodiments of formula I, $R^b$ is hydrogen.
In certain embodiments of formula I, $R^b$ is $C_{1-6}$alkyl.
In certain embodiments of formula I, $R^b$ is halo.
In certain embodiments of formula I, $R^b$ is $C_{1-6}$alkoxy.
In certain embodiments of formula I, $R^b$ is cyano.
In certain embodiments of formula I, $R^b$ is halo-$C_{1-6}$alkyl.
In certain embodiments of formula I, each $R^b$ is independently: hydrogen; fluoro; chloro; or trifluoromethyl.
In certain embodiments of formula I, each $R^b$ is independently: hydrogen; $C_{1-6}$alkyl; or halo.
In certain embodiments of formula I, each $R^b$ is independently: hydrogen; or halo.
In certain embodiments of formula I, each $R^b$ is independently: hydrogen; or fluoro.
In certain embodiments of formula I, each $R^c$ is independently: hydrogen; or $C_{1-6}$alkyl.
In certain embodiments of formula I, $R^c$ is hydrogen.
In certain embodiments of formula I, $R^c$ is $C_{1-6}$alkyl.
In certain embodiments of formula I, $R^c$ is halo.

In certain embodiments of formula I, $R^d$ is: hydrogen; $C_{1-6}$alkyl; $C_{3-6}$cycloalkyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N-$C_{1-6}$alkyl-aminocarbonyl; N,N-di-$C_{1-6}$alkyl-aminocarbonyl; aminosulfonyl; N-$C_{1-6}$alkyl-aminosulfonyl; N,N-di-$C_{1-6}$alkyl-aminosulfonyl; cyano; $C_{1-6}$alkoxy; $C_{1-6}$alkyl-sulfonylamino; amino; N-$C_{1-6}$alkyl-amino; N,N-di-$C_{1-6}$alkyl-amino; halo-$C_{1-6}$alkyl; or hydroxyl; wherein the $C_{1-6}$alkyl moieties may be unsubstituted or substituted one or more times with halo; and wherein the $C_{3-6}$cycloalkyl, and $C_{3-6}$cycloalkyl-$C_{1-6}$alkyl moieties may be unsubstituted or substituted one or more times with $R^g$.

In certain embodiments of formula I, $R^d$ is hydrogen.

In certain embodiments of formula I, $R^d$ is $C_{1-6}$alkyl.

In certain embodiments of formula I, $R^d$ is $C_{3-6}$cycloalkyl which may be unsubstituted or substituted one or more times with $R^g$.

In certain embodiments of formula I, $R^d$ is $C_{3-6}$cycloalkyl-$C_{1-6}$alkyl which may be unsubstituted or substituted one or more times with $R^g$.

In certain embodiments of formula I, $R^d$ is halo.

In certain embodiments of formula I, $R^d$ is $C_{1-6}$alkyl-carbonyl.

In certain embodiments of formula I, $R^d$ is $C_{3-6}$cycloalkyl-carbonyl wherein the $C_{3-6}$cycloalkyl moeity may be unsubstituted or substituted one or more times with $R^g$.

In certain embodiments of formula I, $R^d$ is $C_{3-6}$cycloalkyl-$C_{1-6}$alkyl-carbonyl wherein the $C_{3-6}$cycloalkyl-$C_{1-6}$alkyl moiety may be unsubstituted or substituted one or more times with $R^g$.

In certain embodiments of formula I, $R^d$ is $C_{1-6}$alkyl-sulfonyl.

In certain embodiments of formula I, $R^d$ is $C_{3-6}$cycloalkyl-sulfonyl.

In certain embodiments of formula I, $R^d$ is $C_{3-6}$cycloalkyl-$C_{1-6}$alkyl-sulfonyl.

In certain embodiments of formula I, $R^d$ is aminocarbonyl.

In certain embodiments of formula I, $R^d$ is N-$C_{1-6}$alkyl-aminocarbonyl.

In certain embodiments of formula I, $R^d$ is N,N-di-$C_{1-6}$alkyl-aminocarbonyl.

In certain embodiments of formula I, $R^d$ is aminosulfonyl.

In certain embodiments of formula I, $R^d$ is N-$C_{1-6}$alkyl-aminosulfonyl.

In certain embodiments of formula I, $R^d$ is N,N-di-$C_{1-6}$alkyl-aminosulfonyl.

In certain embodiments of formula I, $R^d$ is cyano.

In certain embodiments of formula I, $R^d$ is $C_{1-6}$alkoxy.

In certain embodiments of formula I, $R^d$ is $C_{1-6}$alkyl-sulfonylamino.

In certain embodiments of formula I, $R^d$ is amino.

In certain embodiments of formula I, $R^d$ is N-$C_{1-6}$alkyl-amino.

In certain embodiments of formula I, $R^d$ is N,N-di-$C_{1-6}$alkyl-amino.

In certain embodiments of formula I, $R^d$ is halo-$C_{1-6}$alkyl.

In certain embodiments of formula I, $R^d$ is hydroxy.

In certain embodiments of formula I, $R^d$ is $C_{3-6}$cycloalkeny which may be unsubstituted or substituted one or more times with $R^g$.

In certain embodiments of formula I, $R^d$ is cyano-$C_{1-6}$alkyl-carbonyl.

In certain embodiments of formula I, $R^d$ is hydroxy-$C_{1-6}$alkyl-carbonyl.

In certain embodiments of formula I, $R^d$ is $C_{1-6}$alkoxy-$C_{1-6}$alkyl-carbonyl.

In certain embodiments of formula I, $R^d$ is carboxy.

In certain embodiments of formula I, $R^d$ is N-cyano-aminocarbonyl.

In certain embodiments of formula I, $R^d$ is N-cyano-N-$C_{1-6}$alkyl-aminocarbonyl.

In certain embodiments of formula I, $R^d$ is N-$C_{1-6}$alkyl-acetimidamidyl.

In certain embodiments of formula I, $R^d$ is N,N'-di-$C_{1-6}$alkyl-acetimidamidyl.

In certain embodiments of formula I, $R^d$ is N'-cyano-N-$C_{1-6}$alkyl-acetimidamidyl.

In certain embodiments of formula I, $R^d$ is N'-hydroxy-acetimidamidyl.

In certain embodiments of formula I, $R^d$ is N'-$C_{1-6}$alkoxy-acetimidamidyl.

In certain embodiments of formula I, $R^d$ is N'-hydroxy-N-$C_{1-6}$alkyl-acetimidamide;

In certain embodiments of formula I, $R^d$ is N'-$C_{1-6}$alkoxy-N-$C_{1-6}$alkyl-acetimidamidyl.

In certain embodiments of formula I, $R^d$ is 2-nitro-1-N-$C_{1-6}$alkylamino-vinyl.

In certain embodiments of formula I, $R^d$ is $C_{1-6}$alkyl-sulfonyl-$C_{1-6}$alkyl.

In certain embodiments of formula I, $R^d$ is N-hydroxy-aminocarbonyl.

In certain embodiments of formula I, $R^d$ is N-$C_{1-6}$alkoxy-aminocarbonyl.

In certain embodiments of formula I, $R^d$ is N-hydroxy-N-$C_{1-6}$alkyl-aminocarbonyl.

In certain embodiments of formula I, $R^d$ is N-$C_{1-6}$alkoxy-N-$C_{1-6}$alkyl-aminocarbonyld In certain embodiments of formula I, $R^d$ is N-$C_{1-6}$alkyl-sulfonylaminocarbonyl.

In certain embodiments of formula I, $R^d$ is N-($C_{1-6}$alkyl-sulfonyl)-N-$C_{1-6}$alkyl-aminocarbonyl.

In certain embodiments of formula I, $R^d$ is heterocyclyl which may be unsubstituted or substituted one or more times with $R^g$.

In embodiments of formula I wherein $R^d$ is heterocyclyl, such heterocyclyl may be oxetanyl, tetrahydrofuranyl, tetrahydropyranyl, azetidinyl, pyrrolidinyl, piperidinyl, azepinyl or piperazinyl, each of which may be unsubstituted or substituted one or more times with $R^g$.

In certain embodiments of formula I, $R^d$ is heteroaryl which may be unsubstituted or substituted one or more times with $R^g$.

In embodiments of formula I wherein $R^d$ is heteroaryl, such heteroaryl may be be pyridinyl, pyrimidinyl, pyrrolyl, imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^g$.

In embodiments of formula I wherein $R^d$ is heteroaryl, such heteroaryl may be be imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^g$.

In certain embodiments of formula I, $R^c$ and $R^d$ together with the atoms to which they are attached form a four, five, six or seven membered ring.

In certain embodiments of formula I, $R^c$ and $R^d$ together with the atoms to which they are attached form a four membered ring.

In certain embodiments of formula I, $R^c$ and $R^d$ together with the atoms to which they are attached form a five membered ring.

In certain embodiments of formula I, $R^c$ and $R^d$ together with the atoms to which they are attached form a six membered ring.

In certain embodiments of formula I, $R^c$ and $R^d$ together with the atoms to which they are attached form a seven membered ring.

In certain embodiments of formula I, $R^e$ is: hydrogen; $C_{1-6}$alkyl; $C_{3-6}$cycloalkyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N-$C_{1-6}$alkyl-aminocarbonyl; N,N-di-$C_{1-6}$alkyl-aminocarbonyl; aminosulfonyl; N-$C_{1-6}$alkyl-aminosulfonyl; or N,N-di-$C_{1-6}$alkyl-aminosulfonyl; wherein the $C_{1-6}$alkyl moieties may be unsubstituted or substituted one or more times with halo; and wherein the $C_{3-6}$cycloalkyl, and $C_{3-6}$cycloalkyl-$C_{1-6}$alkyl moieties may be unsubstituted or substituted one or more times with $R^g$.

In certain embodiments of formula I, $R^e$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N-$C_{1-6}$alkyl-aminocarbonyl; or N,N-di-$C_{1-6}$alkyl-aminocarbonyl; aminosulfonyl; N-$C_{1-6}$alkyl-aminosulfonyl; or N,N-di-$C_{1-6}$alkyl-aminosulfonyl; wherein the $C_{3-6}$cycloalkyl, and $C_{3-6}$cycloalkyl-$C_{1-6}$alkyl moieties each may be unsubstituted or substituted one or more times with $R^g$.

In certain embodiments of formula I, $R^e$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; or $C_{3-6}$cycloalkyl-$C_{1-6}$alkyl-sulfonyl; wherein the $C_{3-6}$cycloalkyl, and $C_{3-6}$cycloalkyl-$C_{1-6}$alkyl moieties each may be unsubstituted or substituted one or more times with $R^g$.

In certain embodiments of formula I, $R^e$ is: $C_{1-6}$alkyl-carbonyl; $C_{3-6}$cycloalkyl-carbonyl; or $C_{3-6}$cycloalkyl-$C_{1-6}$alkyl-carbonyl; wherein the $C_{3-6}$cycloalkyl, and $C_{3-6}$cycloalkyl-$C_{1-6}$alkyl moieties each may be unsubstituted or substituted one or more times with $R^g$.

In certain embodiments of formula I, $R^e$ is hydrogen.

In certain embodiments of formula I, $R^e$ is $C_{1-6}$alkyl.

In certain embodiments of formula I, $R^e$ is $C_{3-6}$cycloalkyl which may be unsubstituted or substituted one or more times with $R^e$.

In certain embodiments of formula I, $R^e$ is $C_{3-6}$cycloalkyl-$C_{1-6}$alkyl.

In certain embodiments of formula I, $R^e$ is $C_{1-6}$alkyl-carbonyl.

In certain embodiments of formula I, $R^e$ is $C_{3-6}$cycloalkyl-carbonyl.

In certain embodiments of formula I, $R^e$ is $C_{3-6}$cycloalkyl-$C_{1-6}$alkyl-carbonyl.

In certain embodiments of formula I, $R^e$ is $C_{1-6}$alkyl-sulfonyl.

In certain embodiments of formula I, $R^e$ is $C_{3-6}$cycloalkyl-sulfonyl.

In certain embodiments of formula I, $R^e$ is $C_{3-6}$cycloalkyl-$C_{1-6}$alkyl-sulfonyl.

In certain embodiments of formula I, $R^e$ is aminocarbonyl.

In certain embodiments of formula I, $R^e$ is N-$C_{1-6}$alkyl-aminocarbonyl.

In certain embodiments of formula I, $R^e$ is N,N-di-$C_{1-6}$alkyl-aminocarbonyl.

In certain embodiments of formula I, $R^e$ is aminosulfonyl.

In certain embodiments of formula I, $R^e$ is N-$C_{1-6}$alkyl-aminosulfonyl.

In certain embodiments of formula I, $R^e$ is or N,N-di-$C_{1-6}$alkyl-aminosulfonyl.

In certain embodiments of formula I, R is $C_{3-6}$cycloalkenyl.

In certain embodiments of formula I, $R^e$ is cyano-$C_{1-6}$alkyl-carbonyl.

In certain embodiments of formula I, R is hydroxy-$C_{1-6}$alkyl-carbonyl.

In certain embodiments of formula I, $R^e$ is $C_{1-6}$alkoxy-$C_{1-6}$alkyl-carbonyl.

In certain embodiments of formula I, $R^e$ is N-cyano-aminocarbonyl.

In certain embodiments of formula I, $R^e$ is N-cyano-N-$C_{1-6}$alkyl-aminocarbonyl.

In certain embodiments of formula I, $R^e$ is N-$C_{1-6}$alkyl-acetimidamidyl.

In certain embodiments of formula I, $R^e$ is N,N'-di-$C_{1-6}$alkyl-acetimidamidyl.

In certain embodiments of formula I, $R^e$ is N'-cyano-N-$C_{1-6}$alkyl-acetimidamidyl.

In certain embodiments of formula I, $R^e$ is N'-hydroxy-acetimidamidyl.

In certain embodiments of formula I, $R^e$ is N'-$C_{1-6}$alkoxy-acetimidamidyl.

In certain embodiments of formula I, $R^e$ is N'-hydroxy-N-$C_{1-6}$alkyl-acetimidamidyl.

In certain embodiments of formula I, $R^e$ is N'-$C_{1-6}$alkoxy-N-$C_{1-6}$alkyl-acetimidamidyl.

In certain embodiments of formula I, $R^e$ is 2-nitro-1-N-$C_{1-6}$alkylamino-vinyl.

In certain embodiments of formula I, $R^e$ is $C_{1-6}$alkyl-sulfonyl-$C_{1-6}$alkyl.

In certain embodiments of formula I, $R^e$ is N-hydroxy-aminocarbonyl.

In certain embodiments of formula I, $R^e$ is N-$C_{1-6}$alkoxy-aminocarbonyl.

In certain embodiments of formula I, $R^e$ is N-hydroxy-N-$C_{1-6}$alkyl-aminocarbonyl.

In certain embodiments of formula I, $R^e$ is N-$C_{1-6}$alkoxy-N-$C_{1-6}$alkyl-aminocarbonyl.

In certain embodiments of formula I, $R^e$ is $C_{1-6}$alkyl-sulfonylamino-$C_{1-6}$alkyl.

In certain embodiments of formula I, $R^e$ is N-($C_{1-6}$alkyl-sulfonyl)aminocarbonyl.

In certain embodiments of formula I, $R^e$ is N-($C_{1-6}$alkyl-sulfonyl)-N-$C_{1-6}$alkyl-aminocarbonyl.

In certain embodiments of formula I, $R^e$ is heterocyclyl which may be unsubstituted or substituted one or more times with $R^g$.

In certain embodiments of formula I, $R^e$ is heteroaryl which may be unsubstituted or substituted one or more times with $R^g$.

In embodiments of formula I wherein $R^e$ is heteroaryl, such heteroaryl may be be pyridinyl, pyrimidinyl, pyrolyl, imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^g$.

In embodiments of formula I wherein $R^e$ is heteroaryl, such heteroaryl may be be imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^g$.

In certain embodiments of formula I, $R^e$ is acetyl.
In certain embodiments of formula I, $R^e$ is methanesulfonyl.
In certain embodiments of formula I, $R^e$ is cyclopropylcarbonyl.
In certain embodiments of formula I, $R^e$ and one of $R^5$ and $R^6$ together with the atoms to which they are attached form a four, five, six or seven membered ring.
In certain embodiments of formula I, $R^e$ and one of $R^5$ and $R^6$ together with the atoms to which they are attached form a four membered ring.
In certain embodiments of formula I, $R^e$ and one of $R^5$ and $R^6$ together with the atoms to which they are attached form a five membered ring.
In certain embodiments of formula I, $R^e$ and one of $R^5$ and $R^6$ together with the atoms to which they are attached form a six membered ring.
In certain embodiments of formula I, $R^e$ and one of $R^5$ and $R^6$ together with the atoms to which they are attached form a seven membered ring.
In certain embodiments of formula I, one of $R^c$ and $R^d$ and one of $R^5$ and $R^6$ together with the atoms to which they are attached form a four, five, six or seven membered ring.
In certain embodiments of formula I, one of $R^c$ and $R^d$ and one of $R^5$ and $R^6$ together with the atoms to which they are attached form a four membered ring.
In certain embodiments of formula I, one of $R^c$ and $R^d$ and one of $R^5$ and $R^6$ together with the atoms to which they are attached form a five membered ring.
In certain embodiments of formula I, one of $R^c$ and $R^d$ and one of $R^5$ and $R^6$ together with the atoms to which they are attached form a six membered ring.
In certain embodiments of formula I, one of $R^c$ and $R^d$ and one of $R^5$ and $R^6$ together with the atoms to which they are attached form a seven membered ring.
In certain embodiments of formula I, $R^g$ is $C_{1-6}$alkyl.
In certain embodiments of formula I, $R^g$ is halo.
In certain embodiments of formula I, $R^g$ is $C_{1-6}$alkoxy.
In certain embodiments of formula I, $R^g$ is halo-$C_{1-6}$alkyl.
In certain embodiments of formula I, $R^g$ is oxo.
In certain embodiments of formula I, $R^g$ is hydroxy.
In certain embodiments of formula I, $R^g$ is acetyl.
In certain embodiments of formula I, $R^h$ is $C_{1-6}$alkyl.
In certain embodiments of formula I, $R^h$ is halo.
In certain embodiments of formula I, $R^h$ is $C_{1-6}$alkoxy.
In certain embodiments of formula I, $R^h$ is halo-$C_{1-6}$alkyl.
In certain embodiments of formula I, $R^h$ is oxo.
In certain embodiments of formula I, $R^h$ is hydroxy.
In certain embodiments of formula I, $R^h$ is acetyl.
In certain embodiments of formula I, the subject compounds may be of formula II:

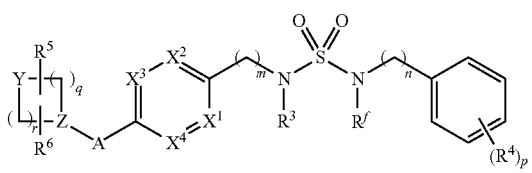

wherein m, n, p, q, r, A, $X^3$, $X^4$, Y, Z, $R^1$, $R^2$, $R^3$, $R^4$, $R^5$, $R^6$ and $R^f$ are as defined herein.
In certain embodiments of formula I, the subject compounds may be of formula III:

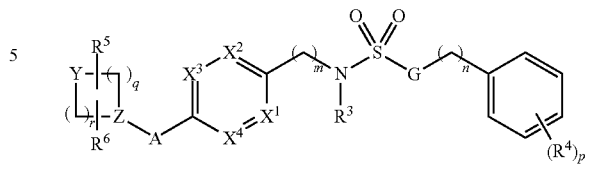

wherein m., n, p, q, r, A, $X^3$, $X^4$, Y, Z, $R^1$, $R^2$, $R^3$, $R^4$, $R^5$ and $R^6$ are as defined herein.
In certain embodiments of formula I, the subject compounds may be of formula IV:

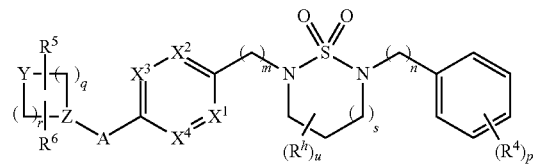

wherein
s is 0, 1 or 2;
u is from 0 to 4; and
wherein m, n, p, q, r, A, $X^3$, $X^4$, Y, Z, $R^3$, $R^4$, $R^5$, $R^6$ and $R^h$ are as defined herein.

Methods

The invention also provides a method for treating a disease or condition mediated by or otherwise associated with the RORc receptor, the method comprising administering to a subject in need thereof an effective amount of a compound of the invention.

The disease may be arthritis such as rheumatoid arthritis or osteoarthritis.

The disease may be asthma or COPD.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I, wherein R is lower alkyl and may be the same or different on each occurrence, $X^-$ is a counterion such as halo, sulfonate, triflate, or the like and may be the same or different on each occurrence, and m, n, p, q, r, A, $X^1$, $X^2$, $X^3$, $X^4$, Y, Z, $R^{1a}$, $R^{2a}$, $R^{1b}$, $R^{2b}$, $R^3$, $R^4$, $R^5$, $R^6$ and $R^f$ are as defined herein.

SCHEME A

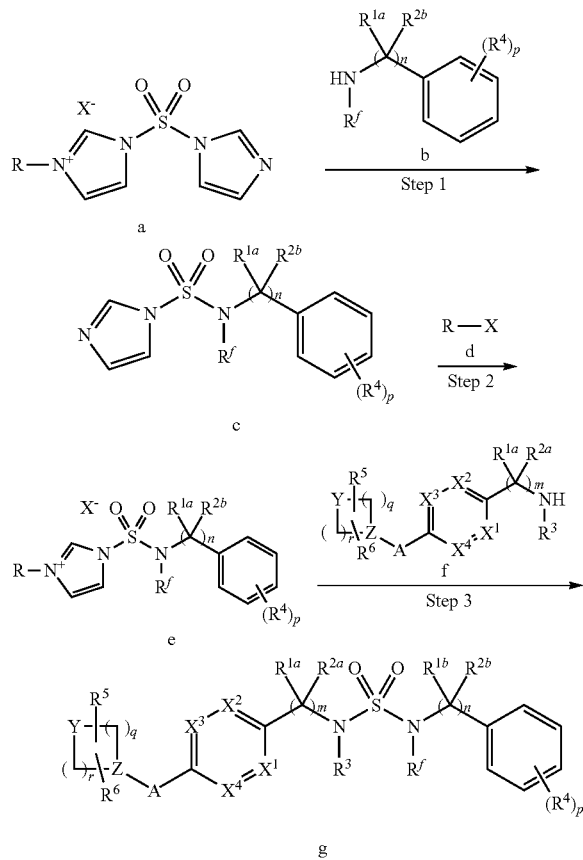

In step 1 of Scheme A, imidazole-sulfonyl)-alkyl-imidazolium salt a is reacted with aryl amine compound b to form imidazole sulfamide compound c. The reaction of step 1 may be carried out in a polar aprotic solvent such as acetonitrile. The counterion of compound a may be triflate and the group R may be methyl in certain embodiments. In certain embodiments the compound a may be prepared by treatment of 1,1'-sulfonyldiimidazole with methyl trifluoromethane sulfonate.

An N-alkylation reaction is carried out in step 2 by reaction of imidazole sulfamide compound c with alkylating reagent d to afford imidazolium sulfamide compound e.

In step 3, imidazolium sulfamide compound e is reacted with aryl amine compound f to yield sulfamide compound g, which is a compound of formula I in accordance with the invention.

Many variations on the procedure of Scheme A are possible and will suggest themselves to those skilled in the art. Specific details for producing compounds of the invention are described in the Examples below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of immune disorders generally. The compounds may be used for treatment of arthritis, including rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

The compounds may be used for treatment of respiratory disorders such as chronic obstructive pulmonary disease (COPD), asthma, bronchospasm, and the like.

The compounds may be used for treatment of gastrointestinal disorder ("GI disorder") such as Irritable Bowel Syndrome (IBS), Inflammatory Bowel Disease (IBD), biliary colic and other biliary disorders, renal colic, diarrhea-dominant IBS, pain associated with GI distension, and the like.

The compounds may be used for treatment of pain conditions such as inflammatory pain; arthritic pain, surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

Examples

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

GENERAL EXPERIMENTAL DETAILS

LCMS Methods:

High Pressure Liquid Chromatography-Mass Spectrometry (LCMS) experiments to determine retention times (RT) and associated mass ions were performed using one of the following methods:

Method A: Compounds were analysed using the following conditions: Experiments were performed on a Waters ZMD single quadrupole mass spectrometer linked to a Hewlett Packard HP1100 LC system with UV diode array detector and 100 position autosampler. The spectrometer has an electrospray source operating in positive and negative ion mode. This system uses a Phenomenex Luna 3 micron C18(2) 30×4.6 mm column at ambient temperature and a 2.0 mL/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. This was maintained for 1 minute before returning to 95% solvent A and 5% solvent B over the next 0.5 minute. Total run time was 6 minutes.

Method B: Compounds were analysed using the following conditions: Experiments were performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7um 100×2.1 mm column, maintained at 40° C. or an Acquity BEH Shield RP18 1.7 μm 100×2.1 mm column, maintained at 40° C. and a 0.4 mL/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minute before returning to 95% solvent A and 5% solvent B over the next 1.2 minutes. Total run time was 8 minutes.

NMR Methods:

$^1$H NMR spectra were recorded at ambient temperature or at 80° C. where indicated using one of the following machines: Varian Unity Inova (400 MHz) spectrometer with a triple resonance 5 mm probe, Bruker Avance DRX 400 (400 MHz) spectrometer with a triple resonance 5 mm probe, a Bruker Avance DPX 300 (300 MHz) equipped with a standard 5 mm dual frequency probe for detection of $^1$H and $^{13}$C, a Bruker AVIII (400 MHz) using a BBI Broad Band Inverse 5 mm probe, or a Bruker AVIII (500 MHz) using a QNP (Quad Nucleus detect) 5 mm probe. Chemical shifts are expressed in ppm relative to an internal standard, tetramethylsilane (ppm=0.00). The following abbreviations have been used: br=broad signal, s=singlet, d=doublet, dd=double doublet, t=triplet, q=quartet, m=multiplet, or any combination of.

Microwave Reactor:

Microwave reactions were carried out using a Biotage® Initiator® in vials appropriate to the scale of the reaction and at the temperature and time described in the experimental details.

Purification Equipment:

Purifications were carried out using pre-packed silica gel cartridges either on a Teledyne ISCO CombiFlash® or Biotage® Isolera Four® or using compressed air to apply external pressure. Solvents and gradients shown in the experimental details were used.

Reverse Phase High Pressure Liquid Chromatography (HPLC) was used to purify compounds where indicated. Separation using gradient elution on a Phenomenex Gemini C18 column (250×21.2 mm, 5 micron) as stationary phase and using mobile phase indicated, operating at a 18 mL/min flow rate using a Gilson UV/Vis-155 dual channel detector and Gilson GX-271 automated liquid handler.

Phase separator cartridges are supplied by Biotage® as Isolute® phase separator cartridges.

LIST OF ABBREVIATIONS

AcOH Acetic acid
AIBN 2,2'-Azobis(2-methylpropionitrile)
Atm. Atmosphere
BOC tert-Butyloxycarbonyl group
(BOC)$_2$O Di-tert-butyl dicarbonate
CDCl$_3$ Deuterated chloroform
DavePhos 2-Dicyclohexylphosphino-2'-(N,N-dimethylamino)biphenyl
DCM Dichloromethane/methylene chloride
DMA N,N-Dimethylacetamide DIAD Diisopropyl azodicarboxylate
DIPEA DIPEA
DMAP 4-Dimethylaminopyridine
DME 1,2-Dimethoxyethane
DMF N,N-Dimethylformamide
DMSO Dimethyl sulfoxide
DPPF 1,1'-Bis(diphenylphosphino)ferrocene
ES Electrospray
Et$_2$O Diethyl ether
Et$_3$N Triethylamine
EtOH Ethanol/Ethyl alcohol
EtOAc Ethyl acetate
HATU 2-(1H-7-Azabenzotriazol-1-yl)-1,1,3,3-tetramethyl uronium hexafluorophosphate methanaminium
HBTU O-Benzotriazol-1-yl-N,N,N',N'-tetramethyluronium hexafluorophosphate
HCl Hydrochloric acid
HOBT 1-Hydroxybenzotriazole
HPLC High pressure liquid chromatography
RP HPLC Reverse phase high pressure liquid chromatography
IBX 2-Iodoxybenzoic acid
IMS Industrial methylated spirit
K$_2$CO$_3$ Potassium carbonate
i-PrOH Isopropanol/isopropyl alcohol/propan-2-ol
LCMS Liquid Chromatograph/Mass Spectroscopy
MeOH Methanol/Methyl alcohol
MW Microwaves
NaH Sodium hydride
NaOH Sodium hydroxide
Na$_2$SO$_4$ Sodium sulfate
Na$_2$CO$_3$ Sodium carbonate
NaHCO$_3$ Sodium bicarbonate/Sodium hydrogen carbonate
NBS N-Bromosuccinimide
NH$_4$Cl Ammonium chloride
NMP 1-Methyl-2-pyrrolidinone
Pd$_2$(dba)$_3$ Tris(dibenzylideneacetone)dipalladium (0)
PSI Pound per square inch
RT Room temperature
sat. Saturated
SCX-2 Pre-packed Isolute® silica-based sorbent with a chemically bonded propylsulfonic acid functional group
TBDMS tert-Butyldimethylsilyl
TFA Trifluoroacetic acid
THF Tetrahydrofuran
TIPS Triisopropyl silyl
TLC Thin layer chromatography
XantPhos 4,5-Bis(diphenylphosphino)-9,9-dimethylxanthene

EXPERIMENTAL PROCEDURES

Example 1

1-(4-fluorobenzyl)-1-isobutyl-3-(4-((1-(methylsulfonyl)piperidin-4-yl)oxy)phenyl)-sulfamide

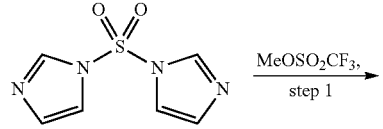

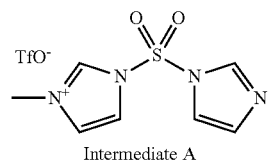

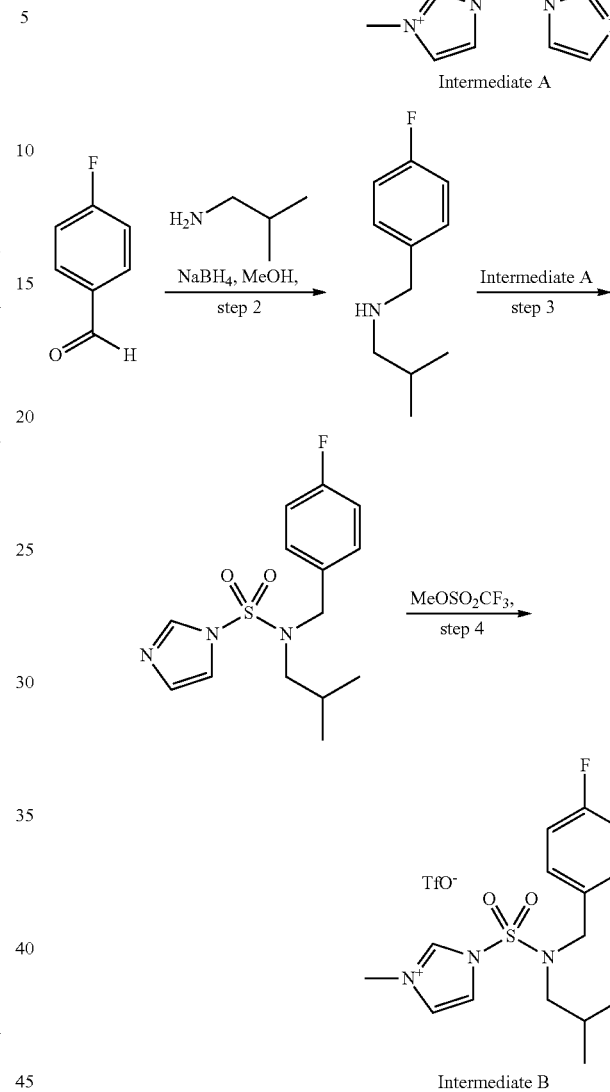

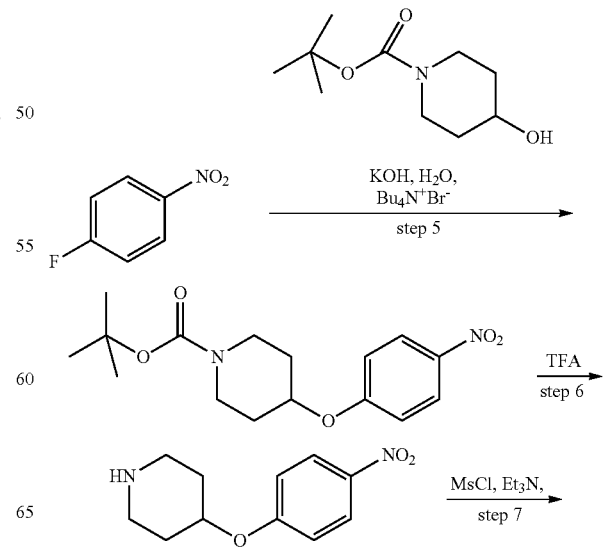

-continued

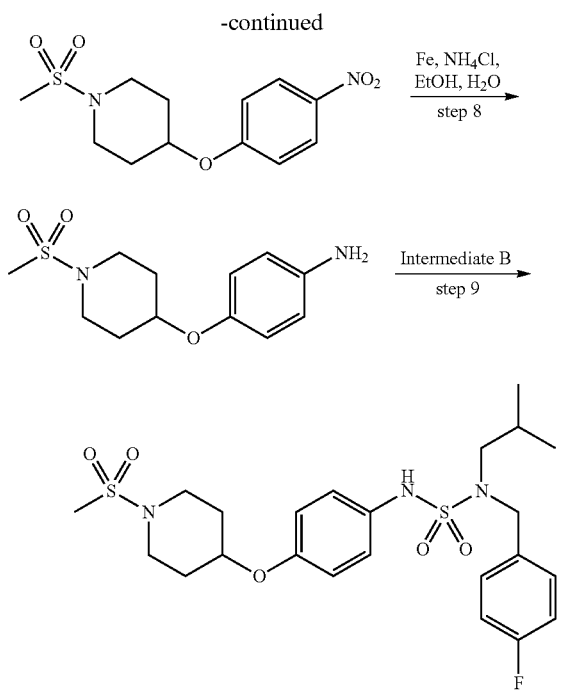

Step 1: 3-(Imidazole-1-sulfonyl)-1-methyl-3H-imidazol-1-ium triflate

A solution of 1,1'-sulfonyldiimidazole (1.50 g, 7.57 mmol) in DCM (25 mL) at 0° C. was treated dropwise with methyl trifluoromethane sulfonate (830 μL, 7.57 mmol) and stirred cold for 3 hours. The precipitate was collected by filtration washing with DCM and air-dried to give the title compound (2.70 g, 98%) as a white solid solid. LCMS (m/z, Method A) ES$^+$ 213.0 [M+1]$^+$.

Step 2: (4-Fluoro-benzyl)-isobutyl-amine

A mixture of 4-fluorobenzaldehyde (6.0 mL, 55.93 mmol), and isobutylamine (3.72 g, 50.85 mmol) in toluene (30 mL) was heated at reflux using Dean-Stark apparatus of 5 hours. The mixture was stood at ambient temperature for 18 hours then cooled in an ice-bath. Sodium borohydride (2.89 g, 76.28 mmol) was added followed by MeOH (5 mL). After 1 hour at 0° C. the reaction was quenched with 1M HCl, basified with a saturated solution of NaHCO$_3$ and extracted into EtOAc (3×). The combined extracts were washed with brine, dried over Na$_2$SO$_4$ and concentrated under vacuum. Purification by silica gel column chromatography (0-10% MeOH in DCM) afforded the title compound (6.98 g, 76%) as a colourless oil. $^1$H NMR (300 MHz, CDCl$_3$) δ 7.28 (m, 2H), 7.00 (m, 2H), 3.74 (s, 2H), 2.42 (d, J=6.8 Hz, 2H), 1.76 (m, 1H), 0.91 (d, J=6.6 Hz, 6H).

Step 3: Imidazole-1-sulfonic acid (4-fluoro-benzyl)-isobutyl-amide

A solution of (4-fluoro-benzyl)-isobutyl-amine (500 mg, 2.76 mmol) in MeCN (20 mL) was treated with 3-(imidazole-1-sulfonyl)-1-methyl-3H-imidazol-1-ium triflate (1.49 g, 4.14 mmol) and heated at reflux for 18 hours. The cooled reaction mixture was concentrated under vacuum and purified by silica gel chromatography (0-50% EtOAc in DCM) to afford the title compound (275 mg, 32%) as a pale yellow oil. $^1$H NMR (300 MHz, CDCl$_3$) δ 7.95 (s, 1H), 7.17 (m, 4H), 7.02 (m, 2H), 4.40 (s, 2H), 3.01 (d, J=7.6 Hz, 2H), 1.77 (m, 1H), 0.80 (d, J=6.6 Hz, 6 H). LCMS (m/z, Method A) ES$^+$ 312.0 [M+1]$^+$.

Step 4: 3-[(4-Fluoro-benzyl)-isobutyl-sulfamoyl]-1-methyl-3H-imidazol-1-ium triflate A solution of imidazole-1-sulfonic acid (4-fluoro-benzyl)-isobutyl-amide (260 mg, 835 μmol) in DCM (5 mL) at 0° C. was treated dropwise with methyl trifluoromethane sulfonate (101 μL, 918 μmol) and stirred cold for 2 hours. The mixture was concentrated under vacuum and used immediately in the next step. LCMS (m/z, Method A) ES$^+$ 326.0 [M+1]$^+$.

Step 5: 4-(4-Nitro-phenoxy)-piperidine-1-carboxylic acid tert-butyl ester

1-Fluoro-4-nitrobenzene (10.0 g, 70.9 mmol) was melted into 4-hydroxy-1-Boc-piperidine (12.97 g, 64.4 mmol). The mixture obtained was treated with a 25 wt % potassium hydroxide solution (60 mL) and tetrabutylammonium bromide (1.60 g, 4.96 mmol) and heated at 40° C. for 70 hours. The precipitate was collected by filtration, washed with water and air-dried to leave the title compound (22.7 g, quantitative yield) as a yellow solid. $^1$H NMR (300 MHz, CDCl$_3$) δ 8.20 (m, 2H), 6.95 (m, 2H), 4.60 (m, 1H), 3.70 (m, 2H), 3.38 (m, 2H), 1.97 (m, 2H), 1.78 (m, 2H), 1.48 (s, 9H).

Step 6: 4-(4-Nitro-phenoxy)-piperidine

A solution of 4-(4-nitro-phenoxy)-piperidine-1-carboxylic acid tert-butyl ester (10.0 g, 31.02 mmol) in DCM (50 mL) was treated with TFA (50 mL) and stirred at ambient temperature for 2 hours. The solvent was removed under vacuum, the residue basified with NH$_4$OH and extracted into DCM (3×). The combined extracts were washed with brine, dried over Na$_2$SO$_4$ and concentrated under vacuum to afford the title compound (7.81 g, quantitative yield) as a yellow residue. $^1$H NMR (300 MHz, CDCl$_3$) δ 8.18 (m, 2H), 6.94 (m, 2H), 4.52 (m, 1H), 3.18 (m, 2H), 2.79 (m, 2H), 2.38 (br s, 1H), 2.05 (m, 2H), 1.72 (m, 2H). LCMS (m/z, Method A) ES$^+$ 223.1 [M+1]$^+$.

Step 7: 1-Methanesulfonyl-4-(4-nitro-phenoxy)-piperidine

A solution of 4-(4-nitro-phenoxy)-piperidine (7.80 g, 35.1 mmol) and triethylamine (7.77 mL, 56.2 mmol) in DCM (100 mL) at 0° C. was treated dropwise with methanesulfonyl chloride (3.26 mL, 42.1 mmol) and stirred cold for 1 hour. The mixture was diluted with DCM, washed with 1M HCl, a saturated NaHCO$_3$ solution, water and brine, dried over Na$_2$SO$_4$ and concentrated under vacuum to leave the title compound (9.10 g, 86% yield) as a yellow/orange solid. $^1$H NMR (300 MHz, CDCl$_3$) δ 8.21 (d, J=9.2 Hz, 2H), 6.97 (d, J=9.2 Hz, 2H), 4.68 (m, 1H), 3.39 (m, 4H), 2.84 (s, 3H), 2.05 (m, 4H). LCMS (m/z, Method A) ES$^+$ 301.0 [M+1]$^+$.

Step 8: 4-(1-Methanesulfonyl-piperidin-4-yloxy)-phenylamine

A mixture of 1-methanesulfonyl-4-(4-nitro-phenoxy)-piperidine (9.07 g, 30.2 mmol), iron powder (~325 mesh, 5.05 g, 90.6 mmol), ammonium chloride solution (6.46 g, 120.8 mmol) in water (50 mL) and EtOH (IMS grade, 150 mL) was heated at reflux for 2 hours. The cooled mixture was filtered through Celite® washing with DCM and the organic solvent removed under vacuum. The remaining aqueous was diluted with water and extracted into DCM (3×). The combined extracts were dried over Na$_2$SO$_4$ and concentrated under vacuum. Purification by silica gel column chromatography (0-10% EtOAc in DCM) followed by trituration from Et$_2$O afforded the title compound (5.71 g, 70%) as an off white solid. $^1$H NMR (300 MHz, DMSO) δ 6.70 (d, J=8.5 Hz, 2H), 6.50 (d, J=8.5 Hz, 2H), 4.65 (br s, 1H), 4.22 (m, 1H), 3.32 (m, 2H), 3.07 (m, 2H), 2.88 (s, 3H), 1.90 (m, 2H), 1.67 (m, 2H). LCMS (m/z, Method A) ES$^+$ 271.0 [M+1]$^+$.

Step 9:: 1-(4-fluorobenzyl)-1-isobutyl-3-(4-((1-(methylsulfonyl)piperidin-4-yl)oxy)phenyl)-sulfamide A mixture of 4-(1-methanesulfonyl-piperidin-4-yloxy)-phenylamine (226 mg, 835 µmol) and 3-[(4-fluoro-benzyl)-isobutyl-sulfamoyl]-1-methyl-3H-imidazol-1-ium triflate (assumed to be 835 µmol) in acetonitrile (10 mL) was heated at 80° C. for 18 hours. The cooled mixture was concentrated under vacuum and purified by silica gel chromatography (0-10% EtOAc in DCM). Further purification by silica gel chromatography (0-100% EtOAc in cyclohexane) followed by trituration from Et$_2$O afforded the title compound (149 mg, 35%) as a white solid. $^1$H NMR (400 MHz, DMSO) δ 9.70 (br s, 1H), 7.28 (dd, J=8.5, 5.6 Hz, 2H), 7.11 (m, 4 H), 6.95 (m, 2H), 4.48 (m, 1H), 4.27 (s, 2H), 3.34 (m, 2H), 3.11 (m, 2H), 2.90 (s, 3H), 2.80 (d, J=7.4 Hz, 2H), 1.99 (m, 2H), 1.74 (m, 2H), 1.58 (m, 1 H), 0.59 (d, J=6.6 Hz, 6H). LCMS (m/z, Method B) ES$^+$ 512.0 [M+1]$^+$.

Example 2

1-(4-fluorobenzyl)-1-isobutyl-3-methyl-3-(4-((1-(methylsulfonyl)piperidin-4-yl)oxy)phenyl)-sulfamid

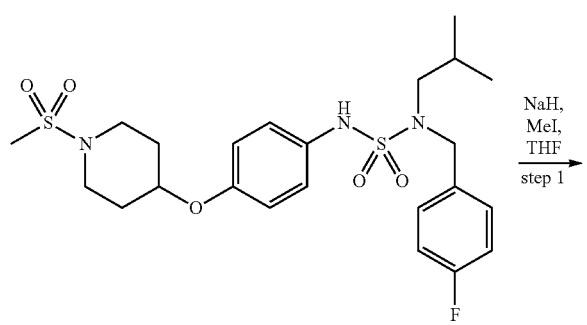

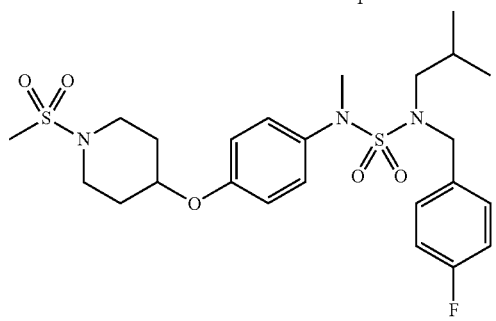

A solution of: 1-(4-fluorobenzyl)-1-isobutyl-3-(4-((1-(methylsulfonyl)piperidin-4-yl)oxy)phenyl)-sulfamide (75 mg, 146 µmol) in THF (3 mL) was treated with NaH (60% dispersion in mineral oil, 9 mg, 219 µmol) and stirred at ambient temperature for 20 minutes. Iodomethane (31 mg, 219 µmol) was added and after 3 hours at ambient temperature the mixture was heated at reflux for 3 hours. Cooled overnight, diluted with EtOAc, washed with water and brine, dried over Na$_2$SO$_4$ and concentrated under vacuum. Purification by silica gel column chromatography (0-100% EtOAc in cyclohexane) followed by trituration from Et$_2$O afforded the 1-(4-fluorobenzyl)-1-isobutyl-3-methyl-3-(4-((1-(methylsulfonyl)piperidin-4-yl)oxy)phenyl)-sulfamide (49 mg, 64%) as a white solid. $^1$H NMR (400 MHz, DMSO) δ 7.35 (m, 4H), 7.16 (t, J=8.8 Hz, 2H), 7.00 (m, 2H), 4.57 (m, 1H), 4.30 (s, 2H), 3.33 (m, 2H), 3.13 (m, 5H), 2.90 (s, 3H), 2.88 (d, J=7.1 Hz, 2H), 1.98 (m, 2H), 1.74 (m, 2H), 1.53 (m, 1H), 0.66 (d, J=6.6 Hz, 6H). LCMS (m/z, Method B) ES$^+$ 527.9 [M+1]$^+$.

Example 3

2-(4-fluorophenyl)-5-(4-((1-(methylsulfonyl)piperidin-4-yl)oxy)benzyl)-1,2,5-thiadiazolidine 1,1-dioxide

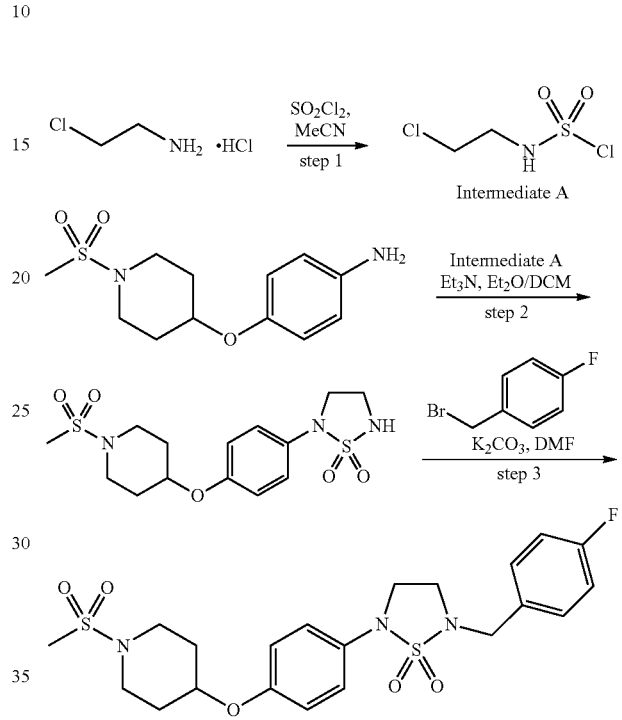

Step 1: Intermediate A, (2-chloroethyl)sulfamoyl chloride

A mixture of 2-chloroethylamine hydrochloride (1.0 g, 8.62 mmol) and sulfuryl chloride (4.19 mL, 51.73 mmol) in acetonitrile (35 mL) was heated at 80° C. for 18 hours. The cooled mixture was concentrated under vacuum, the residue extracted into Et$_2$O (10 mL), the liquors decanted and the insoluble salts removed. The Et$_2$O solution was used immediately in the next reaction.

Step 2: 4-[4-(1,1-Dioxo-1-λ*6*-[1,2,5]thiadiazolidin-2-yl)-phenoxy]-1-methanesulfonyl-piperidine A solution of 4-(1-methanesulfonyl-piperidin-4-yloxy)-phenylamine (500 mg, 1.85 mmol) in diethyl ether (10 mL) and DCM (10 mL) at −70° C. was treated dropwise with the diethyl ether solution of Intermediate A—(2-chloroethyl)sulfamoyl chloride (assumed to be 3.08 mmol). After the addition the mixture was stirred at ambient temperature for 5 hours. The mixture was diluted with DCM, washed with water and brine, dried over Na$_2$SO$_4$ and concentrated under vacuum. Purification by silica gel chromatography (0-100% EtOAc in DCM) afforded the title compound (471 mg, 68%) as an orange residue. $^1$H NMR (300 MHz, CDCl$_3$) δ 7.18 (d, J=8.8 Hz, 2H), 6.87 (m, 2H), 6.45 (br s, 1H), 4.49 (m, 1H), 3.61 (t, J=5.7 Hz, 2H), 3.37 (m, 6H), 2.82 (s, 3H), 2.00 (m, 4H). LCMS (m/z, Method A) ES$^+$ 398.0 [M+Na]$^+$.

Step 3: 2-(4-fluorophenyl)-5-(4-((1-(methylsulfonyl)piperidin-4-yl)oxy)benzyl)-1,2,5-thiadiazolidine 1,1-dioxide A mixture of 4-[4-(1,1-dioxo-1-λ*6*-[1,2,5]thiadiazolidin-2-yl)-phenoxy]-1-methanesulfonyl-piperidine (460 mg, 1.23 mmol), 4-fluorobenzyl bromide (302 mg, 1.60 mmol)

and potassium carbonate (320 mg, 2.32 mmol) in DMF (8 mL) was heated at 100° C. for 18 hours. The cooled mixture was diluted with EtOAc, washed with water (3×) and brine, dried over Na$_2$SO$_4$ and concentrated under vacuum. Purification by silica gel chromatography (0-100% EtOAc in cyclohexane). Further purification by silica gel chromatography (0-10% EtOAc in DCM) followed by trituration from Et$_2$O afforded 2-(4-fluorophenyl)-5-(4-((1-(methylsulfonyl)piperidin-4-yl)oxy)benzyl)-1,2,5-thiadiazolidine 1,1-dioxide (97 mg, 16% yield) as colorless crystalline solid. $^1$H NMR (400 MHz, DMSO) δ 7.46 (dd, J=8.5, 5.6 Hz, 2H), 7.22 (m, 4H), 7.04 (d, J=9.0 Hz, 2H), 4.55 (m, 1H), 4.23 (s, 2H), 3.77 (t, J=6.4 Hz, 2H), 3.31 (m, 4H), 3.12 (m, 2H), 2.90 (s, 3H), 1.98 (m, 2H), 1.73 (m, 2H). LCMS (m/z, Method B) ES$^+$ 483.8 [M+1]$^+$.

Example 4

1-(4-fluorobenzyl)-3-isobutyl-1-methyl-3-(4-((1-(methylsulfonyl)piperidin-4-yl)oxy)phenyl)-sulfamide (342 mg, 40%) as a pale yellow/orange oil. $^1$H NMR (400 MHz, DMSO) δ 7.98 (br s, 1H), 7.25 (m, 4H), 7.08 (m, 2H), 4.26 (s, 2H), 2.75 (s, 3H). LCMS (m/z, Method A) ES$^+$ 270.0 [M+1]$^+$.

Step 2: 1-(4-fluorobenzyl)-1-methyl-3-(4-((1-(methylsulfonyl)piperidin-4-yl)oxy)phenyl)-sulfamide A solution of imidazole-1-sulfonic acid (4-fluoro-benzyl)-methyl-amide (335 mg, 1.24 mmol) in DCM (5 mL) at 0° C. was treated dropwise with methyl trifluoromethane sulfonate (136 μL, 1.24 mmol) and stirred cold for 4 hours. The mixture was concentrated under vacuum and the residue taken up in acetonitrile (5 mL). 4-(1-Methanesulfonyl-piperidin-4-yloxy)-phenylamine (419 mg, 1.55 mmol) was added and the mixture heated at reflux for 18 hours. The cooled mixture was concentrated under vacuum, dissolved in DCM, washed with water and brine, dried over Na$_2$SO$_4$ and concentrated under vacuum. The crude material was purified by silica gel chromatography (0-100% EtOAc in cyclohexane). Further purification by silica gel chromatography (0-10% EtOAc in DCM) followed by trituration from Et$_2$O afforded the title compound (289 mg, 61%) as a white foam. $^1$H NMR (400

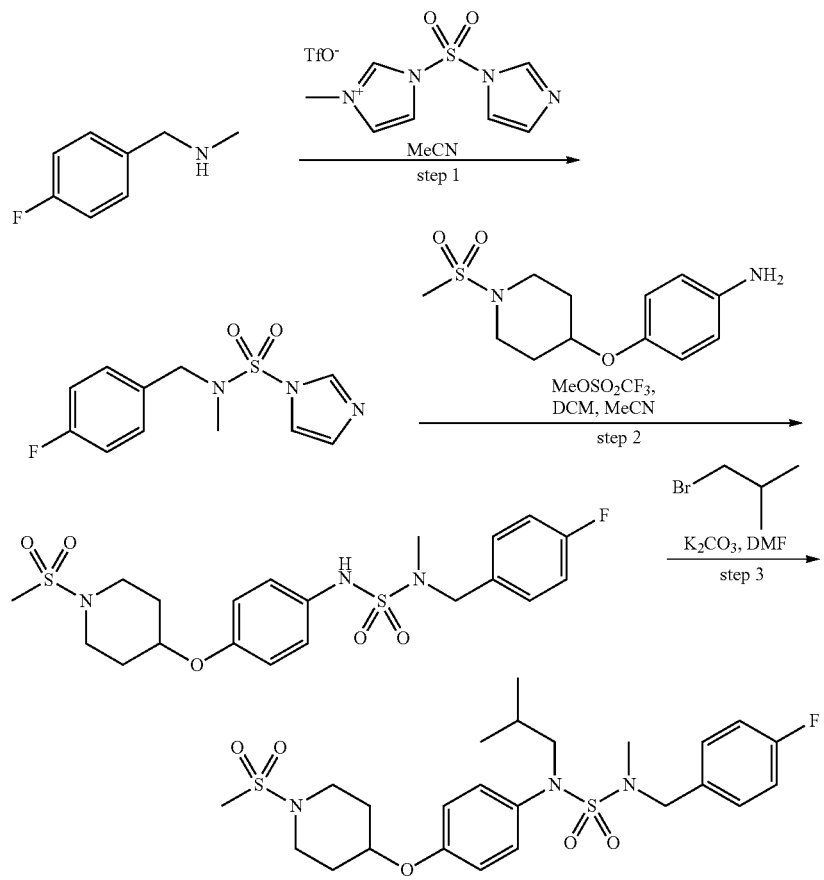

Step 1: Imidazole-1-sulfonic acid (4-fluoro-benzyl)-methyl-amide

A solution of 4-fluoro-N-methylbenzylamine (420 μL, 3.19 mmol) in acetonitrile (10 mL) was treated with 3-(imidazole-1-sulfonyl)-1-methyl-3H-imidazol-1-ium triflate (1.50 g, 4.14 mmol) and stirred at ambient temperature for 5 days. The mixture was concentrated under vacuum and purified by silica gel chromatography to afford the title compound MHz, DMSO) δ 9.71 (br s, 1H), 7.18 (m, 6H), 6.96 (m, 2H), 4.49 (m, 1H), 4.17 (s, 2H), 3.34 (m, 2H), 3.12 (m, 2H), 2.90 (s, 3H), 2.56 (s, 3H), 1.99 (m, 2H), 1.72 (m, 2H). LCMS (m/z, Method B) ES$^+$ 472.0 [M+1]$^+$.

Step 3: 1-(4-fluorophenyl)-3-isobutyl-1-methyl-3-(4-((1-(methylsulfonyl)piperidin-4-yl)oxy)benzyl)-sulfamide A mixture of 1-(4-fluorobenzyl)-1-methyl-3-(4-((1-(methylsulfonyl)piperidin-4-yl)oxy)phenyl)-sulfamide (100 mg, 212 µmol), 1-bromo-2-methyl propane (35 µL, 318 µmol) and K₂CO₃ (59 mg, 424 µmol) in DMF (3 mL) was heated at 110° C. for 4 hours. The cooled mixture was diluted with EtOAc, washed with water (3×) and brine, dried over Na₂SO₄ and concentrated under vacuum. Purification by silica gel chromatography (0-100% EtOAc in cyclohexane) followed by trituration from Et₂O afforded 1-(4-fluorophenyl)-3-isobutyl-1-methyl-3-(4-((1-(methylsulfonyl)piperidin-4-yl)oxy)benzyl)-sulfamide (89 mg, 80%) as a white solid. ¹H NMR (400 MHz, DMSO) δ 7.36 (d, J=8.8 Hz, 2H), 7.24 (dd, J=8.5, 5.6 Hz, 2H), 7.15 (t, J=8.8 Hz, 2H), 7.02 (d, J=8.8 Hz, 2H), 4.58 (m, 1H), 4.15 (s, 2H), 3.36 (m, 4H), 3.13 (m, 2H), 2.90 (s, 3H), 2.58 (s, 3H), 2.01 (m, 2H), 1.74 (m, 2H), 1.46 (m, 1H), 0.86 (d, J=6.6 Hz, 6H). LCMS (m/z, Method B) ES⁺ 528.1 [M+1]⁺.

Example 5

1-(4-(4-acetylpiperazin-1-yl)-2-fluorobenzyl)-1-cyclobutyl-3-methyl-3-phenyl-sulfamide

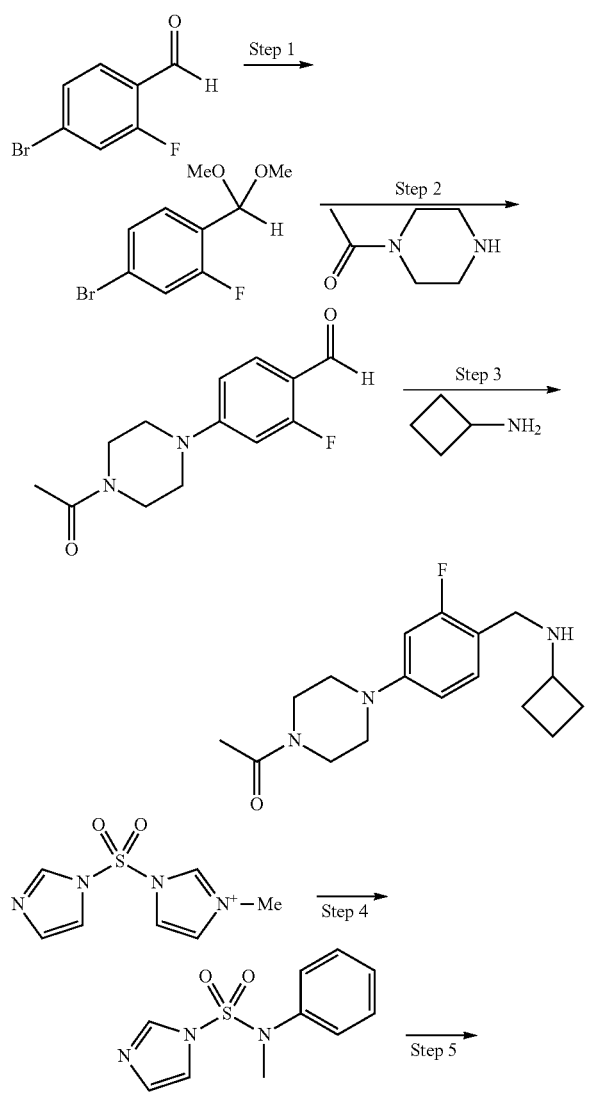

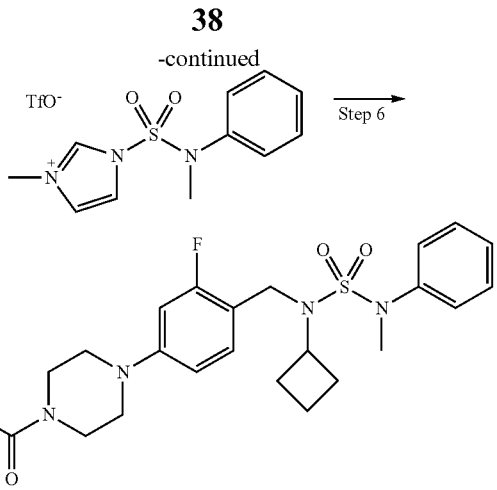

Step 1: 4-Bromo-1-(dimethoxymethyl)-2-fluorobenzene

A solution of 4-bromo-2-fluoro-benzaldehyde (5 g, 24.6 mmol) in a solution of 2 M methanolic HCl (100 mL) was stirred at ambient temperature for 2 hours. The solution was then concentrated and dried under reduced pressure to give the title compound (6.1 g, 99% yield). ¹H NMR (400 MHz, CDCl₃) δ 7.52-7.39 (m, 1H), 7.33-7.27 (m, 1H), 7.27-7.20 (m, 1H), 5.54 (s, 1H), 3.36 (s, 6H).

Step 2: 4-(4-Acetylpiperazin-1-yl)-2-fluorobenzaldehyde

Palladium(II) acetate (111 mg, 0.49 mmol), 2-dicyclohexylphosphino-2',6'-di-i-propoxy-1,1'-biphenyl (469 mg, 0.98 mmol) and sodium tert-butoxide (4.88 g, 49.2 mmol) were combined and the flask was purged with nitrogen. A solution of 1-piperazin-1-ylethanone (4.1 g, 32 mmol) and 4-bromo-1-(dimethoxymethyl)-2-fluoro-benzene (6.13 g, 24.6 mmol) in 1,4-dioxane (82 mL) was then added and the reaction was stirred at 100° C. for 16 hours. The reaction was then filtered through diatomaceous earth and concentrated. The resulting residue was dissolved in 50 mL of THF and 50 mL of 1 N aqueous HCl was added and the reaction was stirred at ambient temperature for 16 hours. The reaction was then neutralized with saturated aqueous Na₂CO₃ and extracted with dichloromethane (×3), dried with MgSO₄, concentrated and purified by silica gel column chromatography (0-10% methanol in dichloromethane) to give 4-(4-acetylpiperazin-1-yl)-2-fluoro-benzaldehyde (3.68 g, 60% yield). LCMS (m/z) ES⁺ 251 [M+1]⁺.

Step 3: 1-(4-(4-((Cyclobutylamino)methyl)-3-fluorophenyl)piperazin-1-yl)ethanone To a solution of cyclobutanamine (1.26 mL, 14.7 mmol) and 4-(4-acetylpiperazin-1-yl)-2-fluoro-benzaldehyde (3.68 g, 14.7 mmol) in dichloroethane (50 mL) was added sodium triacetoxyborohydride (4.39 g, 20.6 mmol) followed by acetic acid (0.84 mL, 14.7 mmol) and the reaction was stirred at ambient temperature for 16 hours. 1 N aqueous NaOH was then added to basify the reaction and the product was extracted with Et₂O (×3), washed with brine, dried with MgSO₄, concentrated and dried in vacuo to give 1-[4-[4-[(cyclobutylamino)methyl]-3-fluoro-phenyl]piperazin-1-yl]ethanone (4.76 g, 99% yield). The product was used without purification. LCMS (m/z) ES⁺ 306 [M+1]⁺.

Step 4: N-methyl-N-phenyl-1H-imidazole-1-sulfonamide

To a solution of 1-(1H-imidazol-1-ylsulfonyl)-3-methyl-1H-imidazol-3-ium trifluoromethanesulfonate (3 g, 8.3 mmol) in dry CH₃CN (dried over MgSO₄) was added N-methylaniline (740 mg, 6.9 mmol) under nitrogen. The mixture was stirred at room temperature for 16 h. After the solvent was removed, the residue was extracted with EtOAc (50 mL×3). The organic layer was washed with brine (50 mL) and water (50 mL). After the solvent was removed, the residue was purified by column chromatography (eluting with 30~60%

EtOAc) to give the title compound, which was used in next step without further purification (1 g, 51%). LCMS (ESI): m/z 237.9 [M+H$^+$].

Step 5: 3-methyl-1-(N-methyl-N-phenylsulfamoyl)-1H-imidazol-3-ium trifluoromethanesulfonate To a solution of N-methyl-N-phenyl-1H-imidazole-1-sulfonamide (700 mg, 2.95 mmol) in dry DCM (5 mL) was added methyl triflate (725 mg, 4.4 mmol) under nitrogen at 0° C. The mixture was stirred at 0° C. for 3 h and at a temperature below 10° C. for 12 h. After the solvent was removed, the residue was used in next step without further purification. LCMS (ESI): m/z 237.9 [M+H$^+$].

Step 6: 1-(4-(4-acetylpiperazin-1-yl)-2-fluorobenzyl)-1-cyclobutyl-3-methyl-3-phenyl-sulfamide To a solution of 1-(4-(4-((cyclobutylamino)methyl)-3-fluorophenyl)piperazin-1-yl)ethanone (HCl salt, 342 mg, 1 mmol) in dry DCM (20 mL) was added 3-methyl-1-(N-methyl-N-henylsulfamoyl)-1H-imidazol-3-ium trifluoromethanesulfonate (700 mg, 1.7 mmol) and DIPEA (0.5 mL) under nitrogen at 0° C. The mixture was warmed to room temperature and stirred for 16 h. The solution was concentrated and purified by prep-TLC and prep-HPLC to give the title compound (50 mg, 10%). $^1$H NMR (400 MHz, CDCl$_3$) δ 7.39-7.26 (m, 6 H), 6.65-6.62 (m, 1 H), 6.51 (dd, J=2.4 Hz, 13.2 Hz, 1 H), 4.34 (s, 2 H), 4.25-4.12 (m, 1 H), 3.76-3.74 (m, 2 H), 3.62-3.59 (m, 2 H), 3.22 (s, 3 H), 3.18-3.12 (m, 4 H), 2.14 (s, 3 H), 2.05-1.89 (m, 4 H), 1.55-1.35 (m, 2 H). LCMS (ESI): m/z 496.9 [M+Na$^+$].

Example 6

Phenyl 4-(4-acetylpiperazin-1-yl)-2-fluorobenzyl (cyclobutyl)sulfamate

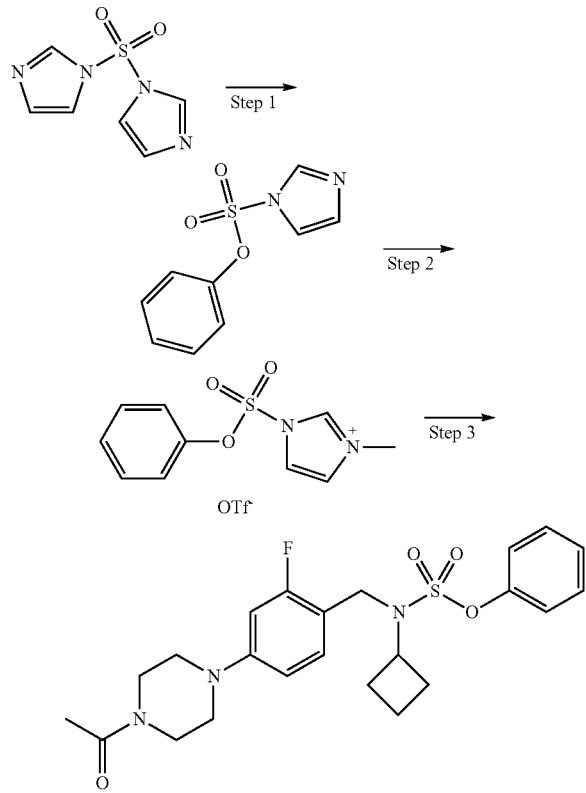

Step 1: Phenyl 1H-imidazole-1-sulfonate

To a solution of phenol (400 mg, 4.3 mmol) in THF (25 mL) was added 1,1'-sulfonyldiimidazole (1.0 g, 5.1 mmol) and Cs$_2$CO$_3$ (2.8 g, 8.5 mmol). The mixture was stirred at ambient temperature for 16 h. The solvent was removed and the residue was purified by silica gel chromatography to yield the title compound (580 mg, 60%).

Step 2: 3-Methyl-1-(phenoxysulfonyl)-1H-imidazol-3-ium triflate

A solution of phenyl 1H-imidazole-1-sulfonate (450 mg, 2.0 mmol) in DCM (15 mL) was treated with methyl triflate (390 mg, 2.4 mmol) at ambient temperature for 16 h. The solvent was removed and the residue was used for next step without further purification.

Step 3: phenyl 4-(4-acetylpiperazin-1-yl)-2-fluorobenzyl(cyclobutyl)sulfamate

To a solution of 3-methyl-1-(phenoxysulfonyl)-1H-imidazol-3-ium triflate (143 mg, 0.6 mmol) and 1-(4-(4-((cyclobutylamino)methyl)-3-fluorophenyl)piperazin-1-yl)ethanone (150 mg, 0.49 mmol) in DCM (20 mL) was added diisopropylethylamine (1 mL). The mixture was stirred at ambient temperature for 16 h. After the solvent was removed, the residue was purified by prep-HPLC to provide the title compound (67.3 mg, 29.6%). $^1$H NMR (400 MHz, DMSO-d$_6$) δ 7.44-7.40 (m, 2 H), 7.34-7.24 (m, 4 H), 6.79-6.67 (m, 2 H), 4.46 (s, 2 H), 4.20-4.17 (m, 1 H), 3.73-3.66 (m, 4 H), 3.26-3.17 (m, 4 H), 2.19-2.15 (m, 2 H), 2.14 (s, 3 H), 2.03-1.98 (m, 2 H), 1.62-1.52 (m, 2 H). LCMS (ESI): m/z 483.9 [M+Na$^+$].

Example 7

1-(4-(4-((1,1-dioxido-7-phenyl-1,2,7-thiadiazepan-2-yl)methyl)-3-fluorophenyl)piperazin-1-yl)ethanone

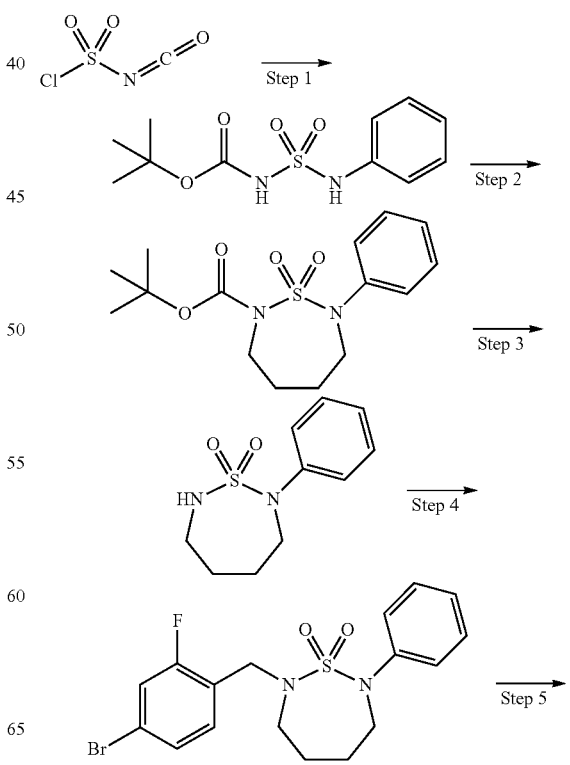

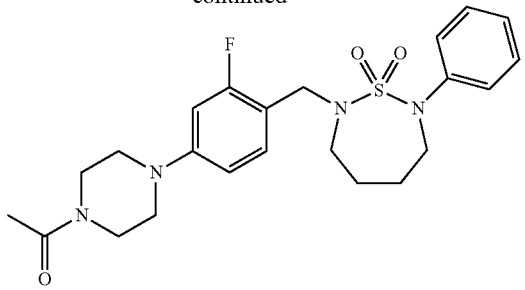

Step 1: tert-Butyl N-Phenylsulfamoylcarbamate

Sulfurisocyanatidic chloride (5.5 g, 39.05 mmol) was dropped into a solution of t-BuOH (2.89 g, 39.05 mmol) in DCM (100 mL) at 0° C., followed by addition of aniline (7.3 g, 78.10 mmol) and triethylamine (7.9 g, 78.10 mmol). The mixture was stirred at ambient temperature for 2 hours. The mixture was washed with water. The organic layer was dried over $Na_2SO_4$ and concentrated under reduced pressure to afford tent-butyl N-phenylsulfamoylcarbamate as white solid (9.5 g, 90%). LCMS (ESI): m/z=272.9 [M+H]$^+$.

Step 2: tert-Butyl 1,1-Dioxo-7-phenyl-1$\lambda^6$,2,7-thiadiazepane-2-carboxylate To a solution of tert-butyl N-phenylsulfamoylcarbamate (2.0 g, 7.35 mmol) and 1,4-dibromobutane (1.6 g, 7.35 mmol) in acetone (30 mL) was added $Cs_2CO_3$ (7.2 g, 22.05 mmol) and the mixture was stirred at 60° C. for 48 hours. The reaction mixture was filtered and concentrated under reduced pressure to afford tert-butyl 1,1-dioxo-7-phenyl-1$\lambda^6$,2,7-thiadiazepane-2-carboxylate as a yellow oil (860 mg, 39%). LCMS (ESI): m/z=271.1 [M−56+H]$^+$.

Step 3: 2-Phenyl-1$\lambda^6$,2,7-thiadiazepane-1,1-dione

A solution of tert-butyl 1,1-dioxo-7-phenyl-1$\lambda$6,2,7-thiadiazepane-2-carboxylate (860 mg, 2.64 mmol) in a 4 M solution of HCl in EtOH (30 mL) was stirred at room temperature for 5 hours. The reaction mixture was concentrated under reduced pressure to afford 2-phenyl-1$\lambda^6$,2,7-thiadiazepane-1,1-dione as a yellow oil (500 mg, 85%). LCMS (ESI): m/z=227.2 [M+H]$^+$.

Step 4: 2-[(4-Bromo-2-fluorophenyl)methyl]-7-phenyl-1$\lambda^6$,2,7-thiadiazepane-1,1-dione A solution of 2-phenyl-1$\lambda$6,2,7-thiadiazepane-1,1-dione (500 mg, 2.21 mmol) and NaH (214 mg, 6.63 mmol) in DMF (15 mL) was stirred at 0° C. for 10 minutes. To the solution was added a solution of 4-bromo-1-(bromomethyl)-2-fluorobenzene (881 mg, 3.32 mmol) in DMF (5 mL) and stirred at room temperature for 3 hours. The reaction mixture was diluted with EtOAc and water, extracted with ethyl acetate, dried over $Na_2SO_4$, filtered, and concentrated under reduced pressure to afford 2-[(4-bromo-2-fluorophenyl)methyl]-7-phenyl-1$\lambda^6$,2,7-thiadiazepane-1,1-dione as a yellow oil (548 mg, 60%). LCMS (ESI): m/z=413.0 [M+H]$^+$.

Step 5: 1-(4-(4-((1,1-dioxido-7-phenyl-1,2,7-thiadiazepan-2-yl)methyl)-3-fluorophenyl)piperazin-1-yl)ethanone A mixture of 2-[(4-bromo-2-fluorophenyl)methyl]-7-phenyl-1$\lambda$6,2,7-thiadiazepane-1,1-dione (200 mg, 0.48 mmol), 1-(piperazin-1-yl)ethanone (93 mg, 0.72 mmol), $Pd_2(dba)_3$ (44 mg, 0.048 mmol), Xant-phos (55 mg, 0.096 mmol), and $Cs_2CO_3$ (469 mg, 1.44 mmol) in 1,4-dioxane (10 mL) under nitrogen atmosphere was stirred at 100° C. for 16 hours. The reaction mixture was filtered and concentrated under reduced pressure. The crude product was purified by preparative HPLC to afford 2-{[4-(4-Acetylpiperazin-1-yl)-2-fluorophenyl]methyl}-7-phenyl-1$\lambda^6$,2,7-thiadiaze-pane-1,1-dione as brown oil (68 mg, 31%). $^1$H NMR (500 MHz, CDCl$_3$) δ ppm 7.35-7.40 (m, 6H), 6.67-6.69 (m, 1H), 6.55-6.58 (m, 1H), 4.50 (s, 2H), 3.76 (t, J=5.5, 2H), 3.60-3.65 (m, 4H), 3.36 (t, J=5.5, 2H), 3.16-3.21 (m, 4H), 2.14 (s, 3H), 1.98 (t, J=5, 2H), 1.90 (t, J=3.5, 2H); LCMS (ESI): m/z=234.9 [M-2-phenyl-1$\lambda^6$,2,7-thiadiazepane-1,1-dione+H]$^+$.

Example 8

1-(4-(3-fluoro-4-((3-methyl-1,1-dioxido-6-phenyl-1,2,6-thiadiazinan-2-yl)methyl)phenyl)piperazin-1-yl)ethanone

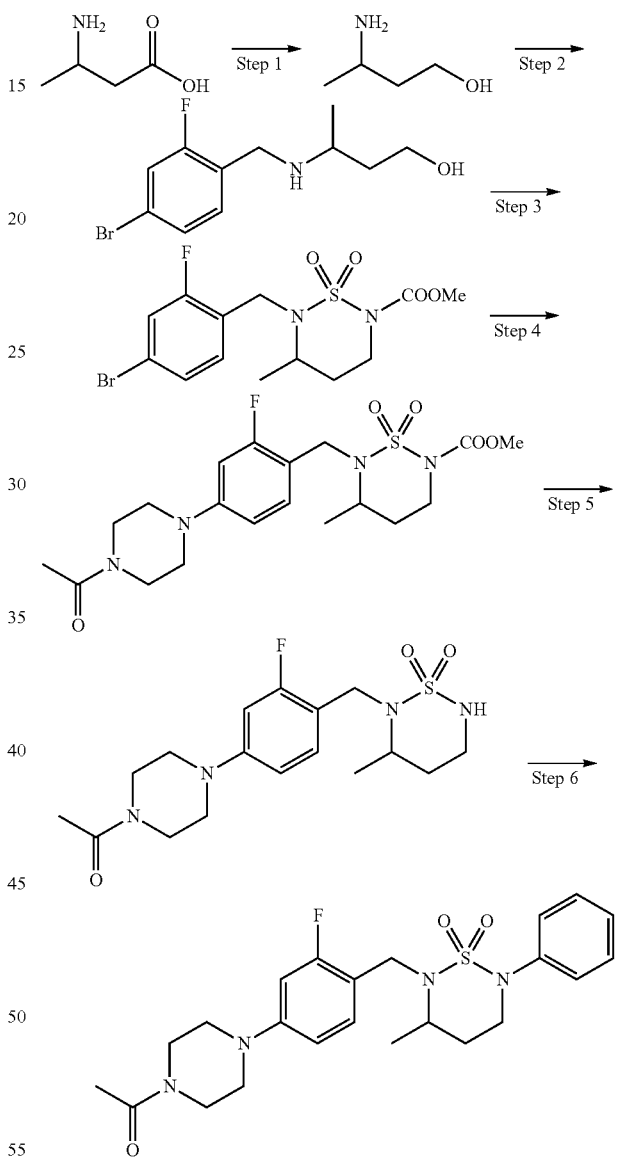

Step 1: 3-Aminobutan-1-ol

To a solution of 3-aminobutanoic acid (2.5 g, 24.3 mmol) in THF at 0° C. was added LiAlH$_4$ (1.9 g, 48.6 mmol) in several small portions. The mixture was heated at 70° C. for 24 hours. The reaction mixture was quenched with $H_2O$ (2.5 mL), NaOH (40%, 2.5 mL), and $H_2O$ (5 mL). The resulting mixture was filtered and washed with THF. The filtrate was concentrated under reduced pressure to afford 3-aminobutan-1-ol as a light yellow oil (2.1 g, 97%). $^1$H-NMR (500 MHz, CDCl$_3$) δ 3.85-3.77 (m, 2H), 3.16-3.10 (m, 1H), 2.42-2.12 (m, 3H), 1.66-1.61 (m, 1H), 1.54-1.46 (m, 1H), 1.16 (d, 3H).

Step 2: 3-(4-Bromo-2-fluorobenzylamino)butan-1-ol

A mixture of 3-aminobutan-1-ol (1.8 g, 20.2 mmol), 4-bromo-2-fluorobenzaldehyde (4.1 g, 20.2 mmol), and $ZnCl_2$ (28 mg, 0.202 mmol) in MeOH (20 mL) was stirred at ambient temperature for 1 hour. To the mixture at 0° C. was added $NaBH_4$ (3.84 g, 101 mmol) and stirred at ambient temperature for 22 hours. The reaction mixture was quenched with $H_2O$ and extracted with EtOAc (30 mL×4). The extracts were combined, washed with brine (20 mL), dried over sodium sulfate, filtered, and concentrated under reduced pressure. The residue was purified by silica gel chromatography using petroleumn ether/EtOAc (5/1) and EtOAc/$NEt_3$ (500/1) as eluting solvents to afford 3-(4-bromo-2-fluorobenzylamino)butan-1-ol as corlorless oil (3.2 g, 57%). $^1$H-NMR (500 MHz, $CDCl_3$) δ 7.25-7.20 (m, 3H), 3.90 (d, 1H), 3.87-3.83 (m, 1H), 3.77-3.173 (m, 2H), 3.00-2.93 (m, 2H), 1.77-1.71 (m, 1H), 1.59-1.52 (m, 1H), 1.20 (d, 3H); LCMS (ESI): m/z=276.1 $[M+H]^+$.

Step 3: Methyl 6-[(4-Bromo-2-fluorophenyl)methyl]-5-methyl-1,1-dioxo-1$\lambda^6$,2,6-thiadi-azinane-2-carboxylate A mixture of 3-(4-bromo-2-fluorobenzylamino)butan-1-ol (800 mg, 2.9 mmol) and Burgess' Reagent (2.07 g, 8.7 mmol) in anhydrous THF (10 mL) was heated at 65° C. for 2 hours. The reaction mixture was concentrated under reduced pressure. The crude product was purified by silica gel chromatography using petroleumn ether/EtOAc (6/1) as eluting solvents to afford methyl 6-[(4-bromo-2-fluorophenyl)methyl]-5-methyl-1,1-dioxo-1$\lambda^6$,2,6-thiadi-azinane-2-carboxylate as light yellow oil. (900 mg, 79%). $^1$H NMR (500 MHz, $CDCl_3$) δ 7.45 (t, 1H), 7.17 (d, 1H), 7.25-7.23 (m, 1H), 4.44 (dd, 2H), 4.20-4.25 (m, 1H), 3.92-3.99 (m, 1H), 3.88 (s, 3H), 3.45-3.51 (m, 1H), 1.87-2.00 (m, 2H), 1.23 (d, 3H); LCMS (ESI): m/z=397.0 $[M+H]^+$.

Step 4: Methyl 6-{[4-(4-Acetylpiperazin-1-yl)-2-fluorophenyl]methyl}-5-methyl-1,1-dioxo-1$\lambda^6$,2,6-thiadiazinane-2-carboxylate A mixture of methyl 6-[(4-bromo-2-fluorophenyl)methyl]-5-methyl-1,1-dioxo-1$\lambda^6$,2,6-thiadiazinane-2-carboxylate (600 mg, 1.5 mmol), 1-(piperazin-1-yl)ethanone (288 mg, 3.0 mmol), $Pd_2(dba)_3$ (138 mg, 0.15 mmol), Xantphos (173 mg, 0.3 mmol), and $Cs_2CO_3$ (978 mg, 3.0 mmol) in 1,4-dioxane (3 mL) was reacted at 100° C. in a microwave oven for 1 hour. The reaction mixture was concentrated under reduced pressure. The residue was purified by silica gel chromatography using petroleumn ether/EtOAc (1/1) as eluting solvents to afford methyl 6-[(4-bromo-2-fluorophenyl)methyl]-5-methyl-1,1-dioxo-1$\lambda^6$,2,6-thiadi-azinane-2-carboxylate as white solid (420 mg, 63%).

Step 5: 2-{[4-(4-Acetylpiperazin-1-yl)-2-fluorophenyl]methyl}-3-methyl-1$\lambda^6$,2,6- thiadiazinane-1,1-dione A mixture of methyl 6-{[4-(4-acetylpiperazin-1-yl)-2-fluorophenyl]methyl}-5-methyl-1,1- dioxo-1$\lambda^6$,2,6-thiadi-azinane-2-carboxylate (420 mg, 0.95 mmol) and NaOH (76 mg, 1.90 mmol) in MeOH/$H_2O$ (1:1, 10 mL) was stirred at 0° C. for 10 minutes and ambient temperature for 2 hours. The reaction mixture was concentrated under reduced pressure. The crude product was purified by reverse phase column chromatography (1% $(NH4)_2CO_3$) to afford 2-{[4-(4-acetylpiperazin-1-yl)-2-fluorophenyl]methyl}-3-methyl-1$\lambda^6$,2,6-thiadiazinane-1,1-dione as white solid (300 mg, 82%). $^1$H NMR (500 MHz, $CDCl_3$) δ 7.42 (t, 1H), 6.68 (dd, 1H), 6.54 (dd, 1H), 4.373 (d, 1H), 4.22 (d, 1H), 3.85-3.90 (m, 1H), 3.76 (t, 2H), 3.61 (t, 2H), 3.53 (dd, 2H), 3.14-3.20 (m, 4H), 2.14 (s, 3H), 1.58-1.67 (m, 2H), 1.23 (d, 3H).

Step 6: 1-(4-(3-fluoro-4-((3-methyl-1,1-dioxido-6-phenyl-1,2,6-thiadiazinan-2-yl)methyl)phenyl)piperazin-1-yl)ethanone A mixture of methyl 2-{[4-(4-acetylpiperazin-1-yl)-2-fluorophenyl]methyl}-3-methyl-1$\lambda^6$,2,6-thiadiazinane-1,1-dione (200 mg, 0.52 mmol), PhI (212 mg, 1.04 mmol), $Pd_2(dba)_3$ (48 mg, 0.052 mmol), Xantphos (60 mg, 0.104 mmol), and $Cs_2CO_3$ (170 mg, 1.04 mmol) in 1,4-dioxane (3 mL) was heated at 100° C. in a microwave oven for 1 hour. The reaction mixture was concentrated under reduced pressure. The crude product was purified by preparative HPLC to afford the title compound as light yellow oil (60 mg, 25%). $^1$H NMR (500 MHz, $CDCl_3$) δ 7.54 (t, 1H), 7.35-7.41 (m, 4H), 7.27-7.29 (m, 1H), 6.69 (dd, 1H), 6.54 (dd, 1H), 4.49 (d, 1H), 4.28-4.35 (m, 2H), 3.90 (td, 1H), 3.76 (t, 2H), 3.61 (t, 2H), 3.53 (td, 1H), 3.14-3.20 (m, 4H), 2.14 (s, 3H), 1.98-2.02 (m, 1H), 1.75-1.78 (m, 1H), 1.25 (d, 3H); LCMS (ESI): m/z=461.7 $[M+H]^+$.

The above compounds, as well as additional compounds made using the above procedures, are shown in Table 1 together with affinity data (micromolar) determined using the procedure of Example 9 below.

TABLE 1

| # | Structure | Name | $IC_{50}$ (μM) |
|---|---|---|---|
| 1 | 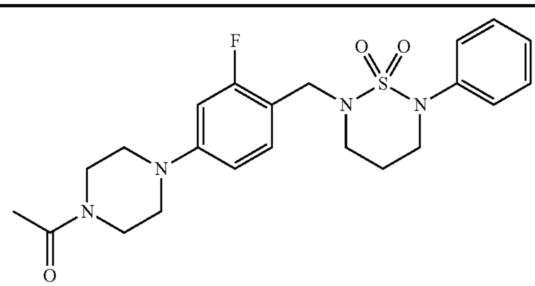 | 1-(4-(4-((1,1-dioxido-6-phenyl-1,2,6-thiadiazinan-2-yl)methyl)-3-fluorophenyl)piperazin-1-yl)ethanone | 0.641 |
| 2 | 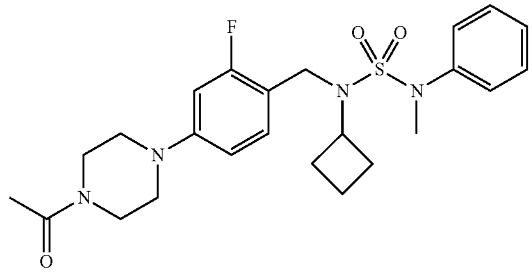 [SMILES: CC(=O)N1CCN(c2ccc(CN(C3CCC3)S(=O)(=O)N(C)c3ccccc3)c(F)c2)CC1] | 1-(4-(4-acetylpiperazin-1-yl)-2-fluorobenzyl)-1-cyclobutyl-3-methyl-3-phenyl-sulfonamide | 0.028 |

TABLE 1-continued

| # | Structure | Name | IC$_{50}$ (μM) |
|---|---|---|---|
| 3 | 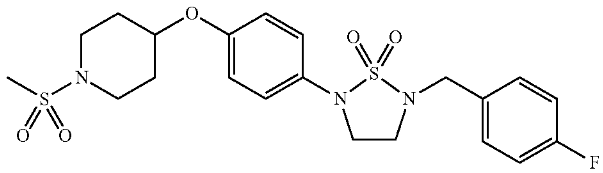 [SMILES: CS(=O)(=O)N1CCC(Oc2ccc(N3CCN(Cc4ccc(F)cc4)S3(=O)=O)cc2)CC1] | 2-(4-fluorobenzyl)-5-(4-((1-(methylsulfonyl)piperidin-4-yl)oxy)phenyl)-1,2,5-thiadiazolidine 1,1-dioxide | 6.42 |
| 4 | 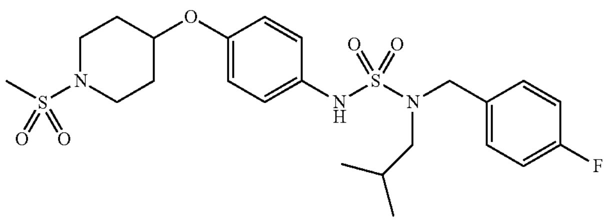 | 1-(4-fluorobenzyl)-1-isobutyl-3-(4-((1-(methylsulfonyl)piperidin-4-yl)oxy)phenyl)-sulfamide | 0.23 |
| 5 | 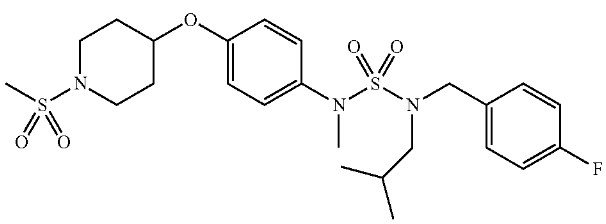 [SMILES: CC(C)CN(Cc1ccc(F)cc1)S(=O)(=O)N(C)c1ccc(OC2CCN(S(C)(=O)=O)CC2)cc1] | 1-(4-fluorobenzyl)-1-isobutyl-3-methyl-3-(4-((1-(methylsulfonyl)piperidin-4-yl)oxy)phenyl)-sulfamide | 0.134 |
| 6 | 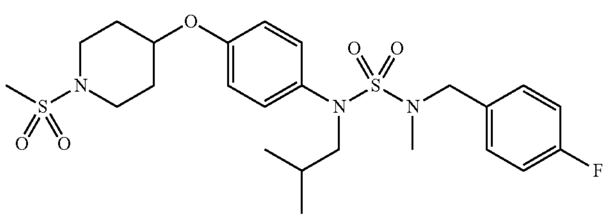 [SMILES: CC(C)CN(c1ccc(OC2CCN(S(C)(=O)=O)CC2)cc1)S(=O)(=O)N(C)Cc1ccc(F)cc1] | 1-(4-fluorobenzyl)-3-isobutyl-1-methyl-3-(4-((1-(methylsulfonyl)piperidin-4-yl)oxy)phenyl)-sulfamide | 0.974 |
| 7 | 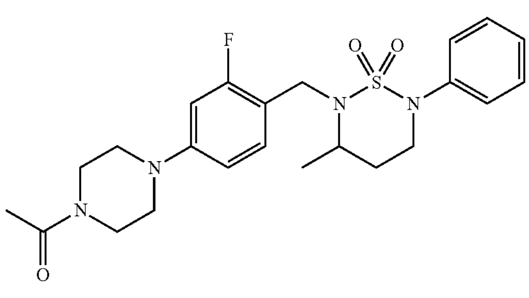 [SMILES: CC(=O)N1CCN(c2ccc(CN3C(C)CCN(c4ccccc4)S3(=O)=O)c(F)c2)CC1] | 1-(4-(3-fluoro-4-((3-methyl-1,1-dioxido-6-phenyl-1,2,6-thiadiazinan-2-yl)methyl)phenyl)piperazin-1-yl)ethanone | 0.096 |
| 8 | 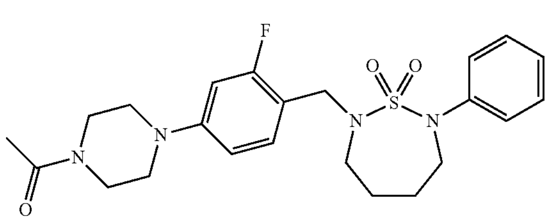 [SMILES: CC(=O)N1CCN(c2ccc(CN3CCCCN(c4ccccc4)S3(=O)=O)c(F)c2)CC1] | 1-(4-(4-((1,1-dioxido-7-phenyl-1,2,7-thiadiazepan-2-yl)methyl)-3-fluorophenyl)piperazin-1-yl)ethanone | 0.045 |

TABLE 1-continued

| # | Structure | Name | IC$_{50}$ (μM) |
|---|---|---|---|
| 9 | 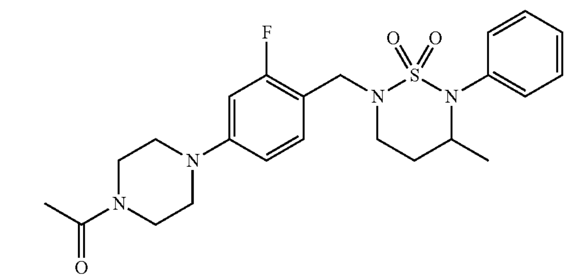 [SMILES: CC(=O)N1CCN(c2ccc(CN3CCC(C)N(c4ccccc4)S3(=O)=O)c(F)c2)CC1] | 1-(4-(3-fluoro-4-((5-methyl-1,1-dioxido-6-phenyl-1,2,6-thiadiazinan-2-yl)methyl)phenyl)piperazin-1-yl)ethanone | 0.48 |
| 10 | 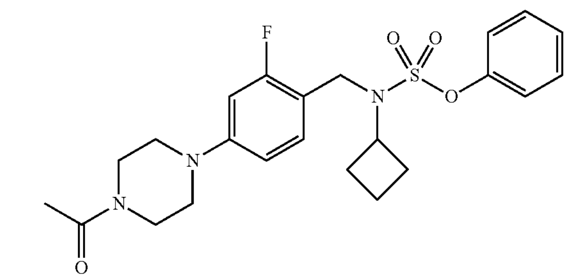 [SMILES: CC(=O)N1CCN(c2ccc(CN(C3CCC3)S(=O)(=O)Oc3ccccc3)c(F)c2)CC1] | phenyl 4-(4-acetylpiperazin-1-yl)-2-fluorobenzyl(cyclobutyl)sulfamate | 0.007 |
| 11 | 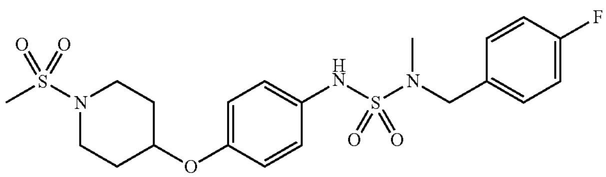 [SMILES: CN(Cc1ccc(F)cc1)S(=O)(=O)Nc1ccc(OC2CCN(S(C)(=O)=O)CC2)cc1] | 1-(4-fluorobenzyl)-1-methyl-3-(4-((1-(methylsulfonyl)piperidin-4-yl)oxy)phenyl)-sulfamide | |

Example 9

In Vitro RORc Ligand Binding Assay

This assay was used to determine a compound's potency in inhibiting activity of RORc by determining, Ki$_{app}$, IC$_{50}$, or percent inhibition values. Consumables used in this Example are shown in Table 5 below.

TABLE 5

| Consumable | Supplier and product code |
|---|---|
| GFB Unifilter plates | Perkin Elmer 6005177 |
| 3-[(3-Cholamidopropyl)dimethylammonio]-1-propanesulfonate (CHAPS) | Sigma C5070 |
| 96-well polypropylene U-bottom assay plate | Nunc 267245 |
| HEPES buffer, 1M | Sigma H3375 |
| Magnesium chloride (MgCl$_2$) | Sigma M8266 |
| D,L-Dithiothreitol (DTT) | Sigma D0632 |
| Sodium chloride (NaCl) | Sigma 71382 |
| Bovine serum albumin (BSA) | Sigma A7030 [lyophilized powder, ≥98% (agarose gel electrophoresis), Essentially fatty acid free, essentially globulin free] |
| 25-hydroxycholesterol | Sigma H1015 |
| 25-[26,27-$^3$H]hydroxycholesterol | Perkin Elmer NET674250UC American Radiolabeled Chemicals ART0766 |
| RORc ligand binding domain | Genentech (e.g., PUR 28048), expressed in *E. coli* |
| Plate seals | Perkin Elmer 6005185 |
| Microscint 0 | Perkin Elmer 6013611 |

Filter Plate Preparation

On day of the assay, 100 uL of 0.05% CHAPS (in deionized H$_2$O) was added to all wells of the GFB Unifilter plate and allowed soak for 1 h. A wash buffer of 50 mM HEPES (pH 7.4), 150 mM NaCl. and 5 mM MgCl$_2$ was prepared to wash the filter plate. To prepare an assay buffer, BSA was added to the wash buffer to reach 0.01% and DTT was added to reach 1 mM.

Compounds

For IC$_{50}$ mode, 10 mM compound stocks were serially diluted in DMSO with DMSO to give 20× required final concentration in DMSO (15 uL compound+30 uL DMSO). The 20× compound stocks were diluted in DMSO with Assay Buffer 4-fold to reach 5× the final test concentration in 25% DMSO (10 uL compound+30 uL Assay Buffer). Solutions were mixed by aspiration several times with a pipette set on 50 uL volume. For the assay, 10 uL of 5× compound stock solutions in 25% DMSO were added to the assay plate in duplicate.

For two point screening, 10 mM stock compound solutions were diluted in DMSO to obtain 200 uM (20× the high test concentration) and then diluted 10-fold further to reach 20 uM (20× the low test concentration). The 20× stocks were diluted 4-fold with Assay Buffer (10 uL compound+30 uL Assay Buffer) to reach 5× the test concentrations (50 uM and 5 uM) and 10 uL were added to two assay plates for the duplicate wells. With each concentration tested on 2 plates, each set of 80 compounds used 4 assay plates (1 uM and 10 uM, with n=2).

Nonspecific Binding (NSB) Samples, Total Binding (TB) Samples and No Receptor (No R) Samples 25-hydroxycholesterol (1 uM) was used to determine the level of NSB signal is prepared in DMSO as for compounds above, then diluted in Assay Buffer to give a final concentration of 5 uM. For 25-hydroxycholesterol in 25% DMSO/75% Assay Buffer; 10 uL per well was used for NSB samples. Wells for Total Binding and No Receptor sample determination contained 10 uL of 25% DMSO/75% Assay Buffer per well.

Radioligand (25-[$^3$H]hydroxycholesterol) Preparation

25-[$^3$H]hydroxycholesterol was dilute in Assay Buffer to obtain 15 nM and vortex to mix. Add 20 uL to all wells to reach 6 nM final in the assay.

Receptor Preparation

The optimal concentration for RORc receptor was found to be 0.6 ug/mL. Stock receptor solution was diluted in assay buffer to obtain 1.5 ug/mL in Assay Buffer. 20 uL was added to all wells. For No R samples, 20 uL Assay Buffer was substituted for receptor solution.

Sample Addition to Plates and Incubation

Assay plates were 96-well polypropylene V-bottom plates. 10 uL of 5× compound in 25% DMSO/75% Assay Buffer was added to Test wells. 10 uL of 25% DMSO/75% Assay Buffer was added to Total Binding or No Receptor wells. 10 uL of 5 uM 25-hydroxycholesterol in 25% DMSO/75% Assay Buffer was added to NSB wells. 20 uL of 15 nM 25-[$^3$H]hydroxycholesterol prepared in Assay Buffer was added to all wells. 20 uL of 1.5 ug/mL RORc receptor was added to wells (or 40 uL Assay Buffer to No R wells). Following addition to the wells, the plates were incubated 3 h at 25° C.

Filtration

Using a Packard Filtermate Harvester, the filter plate were washed 4 times following transfer of the incubated samples. Plates were dry-filtered completely (2 h at 50° C. or overnight at room temperature). 50 uL Microscint 0 was added to all wells and read on Topcount protocol Inverted.

Final Concentrations

Final concentrations were as follows: 50 mM HEPES buffer (pH 7.4); 150 mM NaCl; 1 mM DTT; 5 mM MgCl$_2$; 0.01% BSA; 5% DMSO; 0.6 ug/mL RORc receptor; 6 nM 25-[$^3$H]hydroxycholesterol. For NSB wells, 1 uM 25-hydroxycholesterol was also present.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

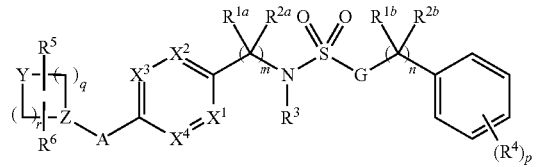

or a pharmaceutically acceptable salt thereof, wherein:
  m is 0 or 1
  n is 0 or 1
  p is from 0 to 3;
  q is 1 or 2;
  r is from 1 to 3;

A is: a bond; —CH$_2$—; —C(O)—; —NR$^a$—; —C(O)NR$^a$—(CH$_2$)$_t$—; —(CH$_2$)$_t$—NR$^a$C(O)—; —O—; —S—; or —SO$_2$—;

t is from 0 to 4;

one of X$^1$, X$^2$, X$^3$ and X$^4$ is N and the others are CR$^b$; or two of X$^1$, X$^2$, X$^3$ and X$^4$ are N and the others are CR$^b$; or three of X$^1$, X$^2$, X$^3$ and X$^4$ are N and the other is CR$^b$; or each of X$^1$, X$^2$, X$^3$ and X$^4$ is CR$^b$;

Y is: —O—; —S—; SO$_2$—; —CR$^c$R$^d$—; or —NR$^e$—;

Z is: CH; or N;

G is: —NR$^f$—; or —O—;

R$^{1a}$, R$^{2a}$, R$^{1b}$ and R$^{2b}$ each independently is: hydrogen; or C$_{1-6}$alkyl which may be unsubstituted or substituted one or more times with halo;

R$^3$ is: hydrogen; C$_{1-6}$alkyl; C$_{3-6}$cycloalkyl; C$_{3-6}$cycloalkyl-C$_{1-6}$alkyl; C$_{1-6}$alkoxy-C$_{1-6}$alkyl; or hydroxy-C$_{1-6}$alkyl, wherein the C$_{1-6}$alkyl and C$_{3-6}$cycloalkyl moieties may be substituted one or more times with halo;

each R$^4$ is independently: C$_{1-6}$alkyl; halo; C$_{1-6}$alkoxy; or cyano; wherein the C$_{1-6}$alkyl moieties may be unsubstituted or substituted one or more times with halo;

R$^5$ is: hydrogen; halo; or C$_{1-6}$alkyl which may be unsubstituted or substituted one or more times with halo;

R$^6$ is: hydrogen; halo; carboxy; C$_{1-6}$alkyl-carbonyl; C$_{1-6}$alkoxy-carbonyl; oxo; hydroxy; aminocarbonyl; N-C$_{1-6}$alkyl-aminocarbonyl; N,N-di-C$_{1-6}$alkyl-aminocarbonyl; or C$_{1-6}$alkyl which may be unsubstituted or substituted one or more times with halo; or oxo;

or R$^5$ and R$^6$ together with the atoms to which they are attached may form a four, five, six or seven membered ring;

R$^a$ is: hydrogen; or C$_{1-6}$alkyl which may be unsubstituted or substituted one or more times with halo;

each R$^b$ is independently: hydrogen; C$_{1-6}$alkyl; halo; C$_{1-6}$alkoxy; or cyano; wherein the C$_{1-6}$alkyl moieties may be unsubstituted or substituted one or more times with halo;

R$^c$ is: hydrogen; halo; or C$_{1-6}$alkyl which may be unsubstituted or substituted one or more times with halo;

R$^d$ is: hydrogen; C$_{1-6}$alkyl; C$_{3-6}$cycloalkyl; C$_{3-6}$cycloalkenyl; C$_{3-6}$cycloalkyl-C$_{1-6}$alkyl; halo; C$_{1-6}$alkyl-carbonyl; C$_{3-6}$cycloalkyl-carbonyl; C$_{3-6}$cycloalkyl-C$_{1-6}$alkyl-carbonyl; cyano-C$_{1-6}$alkyl-carbonyl; hydroxy-C$_{1-6}$alkyl-carbonyl; C$_{1-6}$alkoxy-C$_{1-6}$alkyl-carbonyl; carboxy; N-cyano-aminocarbonyl; N-cyano-N-C$_{1-6}$alkyl-aminocarbonyl; N-C$_{1-6}$alkyl-acetimidamidyl; N,N'-di-C$_{1-6}$alkyl-acetimidamidyl; N'-cyano-N-C$_{1-6}$alkyl-acetimidamidyl; N'-hydroxy-acetimidamidyl; N'-C$_{1-6}$alkoxy-acetimidamidyl; N'-hydroxy-N-C$_{1-6}$alkyl-acetimidamidyl; N-C$_{1-6}$alkoxy-N-C$_{1-6}$alkyl-acetimidamidyl; 2-nitro-1-N-C$_{1-6}$alkylamino-vinyl; formyl; C$_{1-6}$alkyl-sulfonyl; C$_{3-6}$cycloalkyl-sulfonyl; C$_{3-6}$cycloalkyl-C$_{1-6}$alkyl-sulfonyl; C$_{1-6}$alkyl-sulfonyl-C$_{1-6}$alkyl; aminocarbonyl; N-hydroxy-aminocarbonyl; N-C$_{1-6}$alkoxy-aminocarbonyl; N-C$_{1-6}$alkyl-aminocarbonyl; N-hydroxy-N-C$_{1-6}$alkyl-aminocarbonyl; N-C$_{1-6}$alkoxy-N-C$_{1-6}$alkyl-aminocarbonyl; N,N-di-C$_{1-6}$alkyl-aminocarbonyl; aminosulfonyl; N-C$_{1-6}$alkyl-aminosulfonyl; N,N-di-C$_{1-6}$alkyl-aminosulfonyl; cyano; C$_{1-6}$alkoxy; C$_{1-6}$alkyl-sulfonylamino; N-C$_{1-6}$alkyl-sulfonylaminocarbonyl; N-(C$_{1-6}$alkyl-sulfonyl)-N-C$_{1-6}$alkyl-aminocarbonyl; N-(C$_{1-6}$alkyl-sulfonyl)-amino-C$_{1-6}$alkyl; amino; N-C$_{1-6}$alkyl-amino; N,N-di-C$_{1-6}$alkyl-amino; halo-C$_{1-6}$alkyl; heterocyclyl; heteroaryl; or hydroxyl; wherein the C$_{1-6}$alkyl moieties may be unsubstituted or substituted one or more times with halo; and wherein the heterocyclyl, heteroaryl, C$_{3-6}$cycloalkyl, $C_{3-6}$cycloalkenyl and $C_{3-6}$cycloalkyl-$C_{1-6}$alkyl moieties may be unsubstituted or substituted one or more times with $R^g$;

or $R^c$ and $R^d$ together with the atoms to which they are attached may form a four, five, six or seven membered ring that may optionally include one or two heteroatoms selected from —O—, —$NR^a$— or —S—, and which may be optionally substituted one or more times with $R^g$;

$R^e$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; N-cyano-aminocarbonyl; N-cyano-N-$C_{1-6}$alkyl-aminocarbonyl; N-$C_{1-6}$alkyl-acetimidamidyl; N,N'-di-$C_{1-6}$alkyl-acetimidamidyl; N'-cyano-N-$C_{1-6}$alkyl-acetimidamidyl; N'-hydroxy-acetimidamidyl; N'-$C_{1-6}$alkoxy-acetimidamidyl; N'-hydroxy-N-$C_{1-6}$alkyl-acetimidamidyl; N'-$C_{1-6}$alkoxy-N-$C_{1-6}$alkyl-acetimidamidyl; 2-nitro-1-N-$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N-$C_{1-6}$alkoxy-aminocarbonyl; N-$C_{1-6}$alkyl-aminocarbonyl; N-hydroxy-N-$C_{1-6}$alkyl-aminocarbonyl; N-$C_{1-6}$alkoxy-N-$C_{1-6}$alkyl-aminocarbonyl; N,N-di-$C_{1-6}$alkyl-aminocarbonyl; aminosulfonyl; N-$C_{1-6}$alkyl-aminosulfonyl; N,N-di-$C_{1-6}$alkyl-aminosulfonyl; cyano; $C_{1-6}$alkyl-sulfonylamino; $C_{1-6}$alkyl-sulfonylamino-$C_{1-6}$alkyl; N-($C_{1-6}$alkyl-sulfonyl)aminocarbonyl; N-($C_{1-6}$alkyl-sulfonyl)-N-$C_{1-6}$alkyl-aminocarbonyl; N-($C_{1-6}$alkyl-sulfonyl)-amino-$C_{1-6}$alkyl; halo-$C_{1-6}$alkyl; heterocyclyl; or heteroaryl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^g$;

or $R^e$ and one of $R^5$ and $R^6$ together with the atoms to which they are attached may form a four, five, six or seven membered ring that may optionally include one or two additional heteroatom selected from —O—, —$NR^a$— or —S—, and which may be optionally substituted one or more times with $R^g$;

or one of $R^c$ and $R^d$ and one of $R^5$ and $R^6$ together with the atoms to which they are attached may form a four, five, six or seven membered ring that may optionally include an additional heteroatom selected from —O—, —$NR^a$— or —S—, and which may be optionally substituted one or more times with $R^g$;

$R^f$ is: hydrogen; $C_{1-6}$alkyl; $C_{3-6}$cycloalkyl; $C_{3-6}$cycloalkyl-$C_{1-6}$alkyl; $C_{1-6}$alkoxy-$C_{1-6}$alkyl; or hydroxy-$C_{1-6}$alkyl, wherein the $C_{1-6}$alkyl and $C_{3-6}$cycloalkyl moieties may be substituted one or more times with halo;

or $R^f$ and $R^3$ together with the atoms to which they are attached may form a five, six or seven membered ring that may be optionally substituted one or more times with $R^h$;

$R^g$ is: $C_{1-6}$alkyl; halo; oxo; hydroxy; acetyl; or $C_{1-6}$alkoxy; wherein the $C_{1-6}$alkyl moieties may be unsubstituted or substituted one or more times with halo; and $R^h$ is: $C_{1-6}$alkyl; halo; oxo; hydroxy; acetyl; or $C_{1-6}$alkoxy; wherein the $C_{1-6}$alkyl moieties may be unsubstituted or substituted one or more times with halo;

or two of $R^h$ together with the atoms to which they are attached may form a four, five, six or seven membered ring that may optionally include an additional heteroatom selected from —O—, —$NR^a$— or —S—, and which may be optionally substituted one or more times with $R^g$.

2. The compound of claim 1, wherein m is 0.
3. The compound of claim 1, wherein m is 1.
4. The compound of claim 1, wherein n is 0.
5. The compound of claim 1, wherein n is 1.
6. The compound of claim 1, wherein p is 0 or 1.
7. The compound of claim 1, wherein q is 1 and r is 1.
8. The compound of claim 1, wherein q is 2 and r is 2.
9. The compound of claim 1, wherein A is a bond.
10. The compound of claim 1, wherein A is —O—.
11. The compound of claim 1, wherein $X^1$, $X^2$, $X^3$ and $X^4$ are $CR^e$.
12. The compound of claim 1, wherein each $R^b$ is independently:
hydrogen; or halo.
13. The compound of claim 1, wherein Y is —$NR^e$—.
14. The compound of claim 1, wherein Y is —$CR^cR^d$—.
15. The compound of claim 1, wherein Z is CH.
16. The compound of claim 1, wherein Z is N.
17. The compound of claim 1, wherein $R^5$, $R^6$, $R^{1a}$, $R^{1b}$, $R^{2a}$ and $R^{2b}$ are hydrogen.
18. The compound of claim 1, wherein $R^e$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N-$C_{1-6}$alkyl-aminocarbonyl; or N,N-di-$C_{1-6}$alkyl-aminocarbonyl.
19. A composition comprising:
(a) a pharmaceutically acceptable carrier; and
(b) a compound of claim 1.
20. The compound of claim 1, selected from:
1-(4-(4-((1,1-dioxido-6-phenyl-1,2,6-thiadiazinan-2-yl)methyl)-3-fluorophenyl)piperazin-1-yl)ethanone;
1-(4-(4-acetylpiperazin-1-yl)-2-fluorobenzyl)-1-cyclobutyl-3-methyl-3-phenyl-sulfonamide;
2-(4-fluorobenzyl)-5-(4-((1-(methylsulfonyl)piperidin-4-yl)oxy)phenyl)-1,2,5-thiadiazolidine 1,1-dioxide;
1-(4-fluorobenzyl)-1-isobutyl-3-(4-((1-(methylsulfonyl)piperidin-4-yl)oxy)phenyl)-sulfamide;
1-(4-fluorobenzyl)-1-isobutyl-3-methyl-3-(4-((1-(methylsulfonyl)piperidin-4-yl)oxy)phenyl)-sulfamide;
1-(4-fluorobenzyl)-3-isobutyl-1-methyl-3-(4-((1-(methylsulfonyl)piperidin-4-yl)oxy)phenyl)-sulfamide;
1-(4-(3-fluoro-4-((3-methyl-1,1-dioxido-6-phenyl-1,2,6-thiadiazinan-2-yl)methyl)phenyl)piperazin-1-yl)ethanone;
1-(4-(4-((1,1-dioxido-7-phenyl-1,2,7-thiadiazepan-2-yl)methyl)-3-fluorophenyl)piperazin-1-yl)ethanone;
1-(4-(3-fluoro-4-((5-methyl-1,1-dioxido-6-phenyl-1,2,6-thiadiazinan-2-yl)methyl)phenyl)piperazin-1-yl)ethanone;
phenyl4-(4-acetylpiperazin-1-yl)-2-fluorobenzyl(cyclobutyl)sulfamate; and
1-(4-fluorobenzyl)-1-methyl-3-(4-((1-(methylsulfonyl)piperidin-4-yl)oxy)phenyl)-sulfamide.

* * * * *